US012679831B2

(12) United States Patent
Baati et al.

(10) Patent No.: US 12,679,831 B2
(45) Date of Patent: Jul. 14, 2026

(54) THIOPHENOXIME AND FURANOXIME SCAFFOLDS

(71) Applicants: CENTRE NATIONAL DE LA RECHERCHE SCIENTIFIQUE, Paris (FR); Etat français, Service de Santé des Armées représenté par le délégué général de l'armement, Paris (FR); Université de Strasbourg, Strasbourg (FR)

(72) Inventors: Rachid Baati, Strasbourg (FR); Mallikarjuna Reddy Nimmakayala, Strasbourg (FR); José Dias, Brétigny sur Orge (FR); Florian Nachon, Brétigny sur Orge (FR); Camille Voros, Strasbourg (FR); Raymond Franck Razafindrainibe, Schiltigheim (FR)

(73) Assignees: CENTRE NATIONAL DE LA RECHERCHE SCIENTIFIQUE, Paris (FR); Etat français, Service de Santé des Armées représenté par le délégué général de l'armement, Paris (FR); Université de Strasbourg, Strasbourg (FR)

( * ) Notice: Subject to any disclaimer, the term of this patent is extended or adjusted under 35 U.S.C. 154(b) by 556 days.

(21) Appl. No.: 18/044,850

(22) PCT Filed: Sep. 10, 2021

(86) PCT No.: PCT/EP2021/074962
§ 371 (c)(1),
(2) Date: Mar. 10, 2023

(87) PCT Pub. No.: WO2022/053628
PCT Pub. Date: Mar. 17, 2022

(65) Prior Publication Data

US 2023/0357212 A1 Nov. 9, 2023

(30) Foreign Application Priority Data

Sep. 11, 2020 (EP) .................................... 20306010

(51) Int. Cl.

| | |
|---|---|
| ***C07D 409/06*** | (2006.01) |
| ***A61P 39/02*** | (2006.01) |
| ***C07D 407/06*** | (2006.01) |
| ***C07D 519/00*** | (2006.01) |

(52) U.S. Cl.
CPC ............ *C07D 409/06* (2013.01); *A61P 39/02* (2018.01); *C07D 407/06* (2013.01); *C07D 519/00* (2013.01)

(58) Field of Classification Search
CPC .................................................... C07D 409/06
See application file for complete search history.

(56) References Cited

FOREIGN PATENT DOCUMENTS

WO WO-2022023315 A1 * 2/2022 ........... C07D 417/06

OTHER PUBLICATIONS

Henry J. Horstman Fenton et al, "LXXXV.—Derivatives of methylfurfural", Journal of the Chemical Society, Transactions,vol. 79, No. 0, Jan. 1, 1901 (Jan. 1, 1901), p. 807-816.

Lasse J. Nurkkala et al, "The Effects of Pendant vs. Fused Thiophene Attachment upon the Luminescence Lifetimes and Electrochemistry of Tris(2,2'-bipyridine)ruthenium(II) Complexes", European Journal of Inorganic Chemistry,vol. 2008, No. 26, Sep. 1, 2008 (Sep. 1, 2008), p. 4101-4110.

Lasse Nurkkala et al, "Synthesis of the Fused Heterobicycles 5-Pyridin-2-yl-thieno[3,2-b ]pyridine, 6-Pyridin-2-yl-thieno[2,3-b ]pyridine and 6-Pyridin-2-yl-thieno[3,2-c ]pyridine", Synthesis,vol. 2006, No. 8, Apr. 1, 2008 (Apr. 1, 2008), p. 1295-1300.

Andrew O. Stewart et al, "Structure-Activity Relationships of N-Hydroxyurea 5-Lipoxygenase Inhibitors", Journal of Medicinal Chemistry,vol. 40, No. 13, Jun. 1, 1997 (Jun. 1, 1997), p. 1955-1968.

Tatiana S. Ribeiro et al, "The effect of neutral oximes on the reactivation of human acetylcholinesterase inhibited with paraoxon", Journal of the Brazilian Chemical Society,vol. 23, No. 7, Jan. 1, 2012 (Jan. 1, 2012).

Qing Xiao et al, "Facile Assembly of 1-[(Trifluoromethyl)thio]isoquinolines through Reaction of 2-Alkynylbenzaldoxime with Silver (Trifluoromethyl)thiolate : Facile Assembly of 1-[(Trifluoromethyl)thio]isoquinolines", European Journal of Organic Chemistry,vol. 2014, No. 1, Nov. 26, 2013 (Nov. 26, 2013), p. 217-221.

Motion Keith R et al, "Reactions of Diene-conjugated 1.3-Dipolar Intermediates: the Formation of Cyclopropa[c] isoquinolines from Benzonitrile o-Alkenylbenzyl Ylides and their Rearrangements to Benzarepines", Jan. 1, 1992 (Jan. 1, 1992), p. 1709-1719.

Xiao Qian et al, "A Silver(I)-Catalyzed Tandem Reaction of 2-Alkynylbenzaldoxime with Alkylidenecyclopropane", Organic Letters,vol. 14, No. 13, Jul. 6, 2012 (Jul. 6, 2012), p. 3430-3433.

Chemspider, "2-Thiophenecarboxaldehyde, 5-[2-(2-thienyl)ethyl]-, oxime," RegistryJun. 5, 2008 (Jun. 5, 2008), Database accession No. 1025836-13-8.

Chen Yujin et al, "Solution-processable tetrazine and oligothiophene based linear A-D-A small molecules: Synthesis, hierarchical structure and photovoltaic pr", Organic Electronics, Elsevier, Amsterdam, NL,vol. 14, No. 5, Mar. 20, 2013 (Mar. 20, 2013), p. 1424-1434.

(Continued)

*Primary Examiner* — David K O'Dell
(74) *Attorney, Agent, or Firm* — WCF IP

(57) ABSTRACT

The present invention relates to a compound of formula (I). It also relates to a pharmaceutical composition comprising at least one compound of formula (I) and at least one pharmaceutically acceptable support. Finally, it relates to the use of such a compound as a medicine, preferably in the treatment of a nervous and/or respiratory failure due to intoxication with at least one organophosphorous nerve agent; in the treatment of neurological diseases such as Alzheimer's disease; and/or in the treatment of cancer.

5 Claims, No Drawings

(56) References Cited

OTHER PUBLICATIONS

David J. Ager, "The synthesis of 2,5-disubstituted furans", Tetrahedron Letters, vol. 24, No. 49, Jan. 1, 1983 (Jan. 1, 1983), p. 5441-5444.
Katz et al, ChemBioChem. 2015, 16, 2205-2215.
De Koning et al, Eur. J. Med. Chem. 2018, 157,151-160.
Cadieux et al, Chemico-Biological Interactions 2016, 259, 133-141.
Zueva I, Dias J, Lushchekina S, et al. New evidence for dual binding site inhibitors of acetylcholinesterase as improved drugs for treatment of Alzheimer's disease. Neuropharmacology. 2019;155:131-141. doi:10.1016/j.neuropharm.2019.05.025.

* cited by examiner

THIOPHENOXIME AND FURANOXIME SCAFFOLDS

The present invention relates to novel compounds having a thiophenoxime or a furanoxime scaffold. Such compounds may be useful for many therapeutic and non-therapeutic applications. The invention also relates to compositions, notably pharmaceutical compositions, comprising said compounds, and their use.

Organophosphorous nerve agents (OPNA) are extremely toxic compounds that comprise chemical warfare agents (CWA) including sarin, soman, cyclosarin, tabun, methylphosphonothioate (VX) and pesticides such as paraoxon, parathion and tetraethyl pyrophosphate (TEPP). Their acute toxicity results from the irreversible inhibition of acetylcholinesterase (AChE) through phosphylation of its catalytic serine, which results in the inability of the enzyme to hydrolyze acetylcholine (ACh). Accumulation of this neurotransmitter at cholinergic synapses occurs, leading to a permanent saturation of the muscarinic and nicotinic receptors which ultimately results in seizure and respiratory arrest. Depending on the class of OPNA and on the administrated dose, death can occur within a few minutes.

Due to the similarity between the chemical precursors of CWA and pesticides, and to the relatively simple chemistry involved in their synthesis, efforts to control the proliferation of these agents have proved of limited success. Therefore, the development of effective measures to counteract OPNA poisoning remains a challenging issue to protect and treat both civilian and military populations. The current treatment for OPNA poisoning consists in the administration of a combination of atropine (antimuscarinic agent) and diazepam (anticonvulsant drug), to limit convulsions, and of a standard pyridinium oxime (pralidoxime, trimedoxime, HI-6, obidoxime, or HLö-7) to reactivate AChE. Oximes exert their action on OPNA-inhibited AChE by attacking the phosphorous atom of the phosphylated serine, leading to the removal of the phosphonate and restoration of the enzyme's catalytic activity. However, it has been demonstrated that the current therapy results in unequal efficiency, and none of these oximes offer broad efficacy across the different OPNAs. Further limitations of oxime-based therapy include inability to cross the blood-brain barrier (BBB), inability to reactivate the "aged" enzyme, and rapid clearance from the circulation when tested in vivo. Animal model studies and recent clinical trials using pesticide poisoned individuals have shown uneven clinical benefits of these oximes, and even harm, so their true efficacy as antidotes has been debated at the World Health Organisation.

To overcome the disadvantages of the current medication, the development of new broad spectrum and bioavailable centrally active drugs is of crucial importance.

Over the past decades, there has been a growing interest in the development of non-ionic oximes reactivators of OPNA-inhibited hAChE (human AChE) to increase BBB permeability. For example, uncharged hybrid reactivators bearing 3-hydroxy-2-pyridinaldoxime as nucleophilic moiety and a peripheral site AChE ligand, exhibited increased affinity for the phosphylated enzyme, a large spectrum of reactivation and the ability to cross efficiently the BBB in vitro. Beside these discoveries, others heterocyclic, aromatic and acyclic nucleophilic oximes, as well as uncharged acetamido bis-oximes have been developed as antidotes, with more or less success in the reactivation of OPNA-inhibited AChE.

Recently, unusual non-oxime non-ionic new functional groups such as Mannich phenols that are capable of reactivating OPNA-inhibited AChE have been reported by Katz, Cadieux and De Koning (Katz et al, *ChemBioChem.* 2015, 16, 2205-2215; de Koning et al, *Eur. J. Med. Chem.* 2018, 157,151-160; Cadieux et al, *Chemico-Biological Interactions* 2016, 259, 133-141). However, the mechanism of the reactivation is still unclear, and the development of these molecules is hampered by their low stability in biological media.

Recent findings have demonstrated the ability of a zwitterionic, centrally acting, brain penetrating oxime to reverse severe symptoms and rapidly reactivate sarin- and paraoxon inhibited AChE in vivo.

It is further obvious that the above-mentioned compounds are accessed only after tedious, non-flexible and lengthy multistep chemical synthesis due to their increased structural complexity.

Despite these innovative strategies for the development of reactivators, efforts towards shorter and more convergent synthetic routes to innovative broad spectrum and centrally effective antidotes are still needed. There is thus a remaining need for chemical compounds efficient in therapeutic applications, particularly against OPNA intoxications, with a broad spectrum and centrally effective. These compounds have to be quick and easy to synthetize.

Surprisingly, the inventors have now discovered that specific compounds, having a diazinoxime scaffold, fulfill these needs.

Indeed, such compounds are quick and very easy to produce thanks to a late-stage Sonogashira cross-coupling reaction, which leads to a short and expedient synthesis, without using protecting groups for the sensitive oximes. The compounds present very interesting properties: they have a low molecular weight, and exhibit a quite simple molecular structural design and a broad spectrum of reactivation of OPNA-inhibited AChE, especially with increased efficacy for VX and paraoxon.

Notably, these compounds may be used as antidotes against OPNA intoxications or as detoxifying or decontamination agents against organophosphorus compounds, or as sensors for OPNA detection, thanks to their effective and fast reactivation of hAChE without denaturing the same. They may also be used in the treatment of neurodegenerative diseases such as Alzheimer's disease. Finally, particularly the oxime compounds of the invention may be used as histone deacetylases (HDAC) inhibitors; consequently, they may be used in the treatment of cancer.

Thus, a first object of the present invention is a compound of formula (I):

(I)

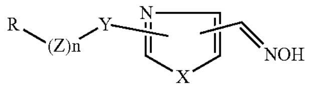

wherein the different groups are as defined in the detailed description below.

Another object of the present invention is a process for preparing the compounds of formula (I), especially by a Sonogashira reaction, as detailed below.

Another object of the present invention is a pharmaceutical composition comprising at least one compound of formula (I) and at least one pharmaceutically acceptable support.

Another object of the invention is a compound according to the invention, for use as a medicine.

A further object of the invention is a compound according to the invention for use in the treatment of a nervous and/or respiratory failure due to intoxication with at least one organophosphorous nerve agent.

Still a further object of this invention is a compound according to the invention for use in the treatment of neurological diseases such as Alzheimer's disease.

Still a further object of this invention is a compound according to the invention for use in the treatment of cancer.

A first object of the present invention is a compound of (I), or one of its pharmaceutically acceptable salts:

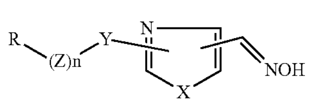

(I)

wherein:

X is S or O;

Y is $-CH_2-CH_2-$, $-C{\equiv}C-$ or $-CH{=}CH-$;

Z is $-CH_2-$;

n is an integer from 0 to 3; and

R is an alkyl group, a heteroalkyl, an aryl, a heteroaryl, a heterocycloalkyl, a biomolecule, a carboxyl group, a hydroxyl group, a cyano, an oxime, an hydroxamic group, a ketone, a thiol or thioether or thioester group, a phosphate, a phosphonate, phosphinate, phosphonium, sulfone, sulfonium, sulfate group, a fluorescent probe, or a group —N(R1)(R2), wherein R1 and R2 are each independently H, an alkyl group, an aryl, a heteroaryl or a group

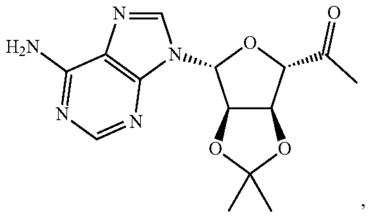 [SMILES: CC(=O)[C@H]1O[C@@H](n2cnc3c(N)ncnc32)[C@@H]2OC(C)(C)O[C@@H]21]

, or R1 and R2 form together with the nitrogen atom a dioxoindolinyl group.

When X is S, then formula (I) is a thiophenoxime scaffold.

When X is O, then formula (I) is a furanoxime scaffold.

By "pharmaceutically acceptable salt", it is meant any salt of a compound of formula (I) with an acid or a base. Preferably, the pharmaceutically acceptable salt is a chlorhydrate salt (also called hydrochloride). Such a salt may be obtained by using HCl. More preferably, the heteroaryl group of R comprises a nitrogen atom, which is complexed with HCl.

Preferably, the compound of the invention is a salt of a compound of formula (I), more preferably a chlorhydrate salt of a compound of formula (I).

The compound of formula (I) may be labeled with one or more isotopes such as $^{15}N$, $^{18}O$, 2H or $^{3}H$. Preferably the compound is labeled on the =N—OH group, with $^{15}N$. Indeed, such a stable, non-toxic and non-radioactive isotope would allow in vivo and in vitro biological studies and profiling.

By "alkyl", it is meant a linear hydrocarbon group preferably comprising from 1 to 20 carbon atoms, in particular from 1 to 15 carbon atoms, or a branched or cyclic hydrocarbon group comprising from 3 to 20 carbon atoms. Examples of alkyl groups include methyl, ethyl, n-propyl, isopropyl, n-butyl, isobutyl, tert-butyl, n-pentyl, isopentyl, n-hexyl, n-tridecyl, cyclohexyl and cyclohexylmethyl groups, and preferably ethyl, propyl, n-hexyl, n-tridecyl, cyclohexyl or cyclohexylmethyl group.

By "heteroalkyl", it is meant a heteroatom that is linked to any alkyl group. The heteroatom may be nitrogen, oxygen, sulfur, phosphorous or boron. A preferred heteroalkyl group is an alkoxy group. By "alkoxy", it is meant an oxygen linked to any alkyl group (—O-alkyl).

By "aryl", it is meant a monocyclic or polycyclic aromatic hydrocarbon group, which may be optionally substituted. Preferably, the aryl group is a phenyl, or a polycyclic aromatic hydrocarbon (PAH). A preferred PAH is pyrene. The aryl is preferably not substituted.

By "heteroaryl", it is meant an aryl group in which at least one carbon atom of the aromatic ring is substituted by a heteroatom, and which may be optionally substituted. The heteroatom may be nitrogen, oxygen, phosphorus or sulfur. Preferably the heteroatom is nitrogen. Examples of heteroaryl groups include pyridine, pyrrole, thiophene, furane, pyrimidine, pyrazine, pyridazine, triazole, tetrazine, triazine, imidazole, quinoline, thiazole, oxetane, oxazole, tetrazole, oxadiazole, thiadiazole, pyrazole, imidazole, triazole, and isoxazole groups. Preferably, the heteroaryl group is a pyridine group such as 2-, 3- or 4-pyridino, more preferably a 3-pyridino; or a quinoline group such as a 4-quinolinyl. The heteroaryl is preferably not substituted. Alternatively, the heteroaryl is substituted, preferably by an alkyl group, preferably methyl, or by a hydroxyl group (—OH).

A "heterocycloalkyl" refers to a non-aromatic saturated monocyclic or polycyclic ring comprising carbon and hydrogen atoms, in which at least one carbon atom of the ring is substituted by a heteroatom. The heteroatom may be nitrogen, oxygen, or sulfur. Preferably, the heterocycloalkyl group is a monocyclic ring comprising from 3 to 6, preferably from 4 to 6 carbon atoms. Preferably, the heterocycloalkyl group is an epoxide, morpholino, pyrazolidine, oxathiolane, tetrahydrofuran, dioxolane, piperidine, piperazine, thiomorpholine, tetrahydropyrane, oxetane or azetidine, such as 4-tetrahydropyrano or 3-oxetano or 3-azetidino. The heterocycloalkyl may be substituted or not.

By "biomolecule", it is meant a sugar moiety, a peptide moiety, an antibody, a virus, a DNA, a RNA or a protein moiety. The sugar moiety may be for example a glucose, fructose or sucrose moiety. A peptide moiety is a moiety typically comprising 1 to 50 amino acids. A protein moiety is a moiety typically comprising at least 51 amino acids, preferably from 60 to 500 amino acids.

By "carboxyl group", it is meant a —COOH group.

By "cyano", it is meant a —CN group.

By "oxime", it is meant a —C(R')=N—OH group, wherein R' is H, an alkyl group or an amine group —NR3R4, wherein R3 and R4 are each H or an alkyl group. When R' is —NR3R4, then the oxime is an amidoxime group.

By "hydroxamic group", it is meant a R5-C(O)—N(OH)— or —C(O)—N(OH)—R5 group, wherein R5 is H or an alkyl group.

By "ketone", it is meant a group comprising the moiety —CO—.

By "thiol, thioether or thioester group", it is respectively meant a group comprising a moiety —SR6, wherein R6 is respectively H, alkyl or —CO—R7, wherein R7 is an alkyl group.

By hydroxyl group, it is meant a group —OH.

By "phosphonate", it is meant a group —P(O)$(OR8)_2$, wherein R8 are identical or different and are either H or an alkyl group. When both R8 are H, then the group is a phosphate, i.e. a group —P(O)$(OH)_2$.

By "phosphinate", it is meant a group —P(O)(OR9), wherein R9 is H or an alkyl group.

By "phosphonium", it is meant a cation $P(R10)_4^+$, wherein each R10 (identical or different) is an alkyl group.

By "sulfone", it is meant a group comprising a radical —SO2.

By "sulfonium", it is meant a cation $S(R11)_3^+$, wherein each R11 (identical or different) is an alkyl group.

By "sulfate group", it is meant —SO4.

By "fluorescent probe", it is meant a chemical function or a fluorophore endowed with fluorescent properties. The fluorescent moiety may be for example a fluoresceine, boron dipyrromethene (BODIPY), a coumarine, a cyanine, an Alexa Fluor, an acridine, a fluorone, a squaraine, a phenanthridine, a cyanine, an oxazine, a perylene, an anthracene or rhodamine moiety.

By «dioxoindolinyl group», it is meant the group

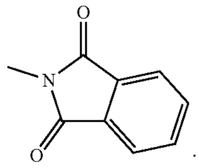
.

Preferably, R is a heteroaryl, an aryl or a group —N(R1)(R2), wherein R1 and R2 are each independently H or a heteroaryl or a group

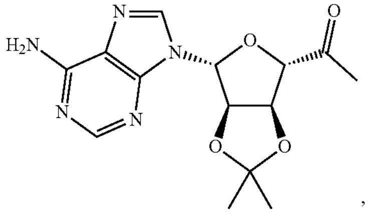 [SMILES: CC(=O)[C@H]1O[C@@H](n2cnc3c(N)ncnc32)[C@@H]2OC(C)(C)O[C@@H]21]
, or R1 and R2 form together with the nitrogen atom a dioxoindolinyl group. Preferably, the heteroaryl group is a pyridine group such as 2-, 3- or 4-pyridino, or a quinoline group such as a 4-quinolinyl, or an imidazolyl group preferably 5-imidazolyl, which is preferably substituted by an alkyl group, preferably methyl; or is a 3-oxetanyl group, preferably substituted by a hydroxyl group (—OH).

Preferably, R is a pyridine group such as 2-, 3- or 4-pyridino, more preferably 3-pyridino. Preferably, according to another embodiment, R is a group —N(R1)(R2), wherein R1 is H, and R2 is a heteroaryl, preferably a quinoline group such as a 4-quinolinyl.

Preferably R is 3-pyridino, a 5-imidazolyl which is substituted by a methyl, a 3-oxetanyl group substituted by a hydroxyl group or a phenyl; or R is a group —N(R1)(R2), wherein R1 and R2 are each independently H, a heteroaryl or a group

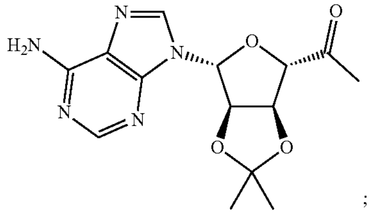 [SMILES: CC(=O)[C@H]1O[C@@H](n2cnc3c(N)ncnc32)[C@@H]2OC(C)(C)O[C@@H]21]
;

or R1 and R2 form together with the nitrogen atom a dioxoindolinyl group.

Preferably, the —Y—(Z)n—R group is in position 5.

According to a first embodiment, the oxime group is in position 2, X is S and the compound of the invention is a 5-substituted-thiophen-2-oxime of formula (II), or one of its pharmaceutically acceptable salts:

(II)

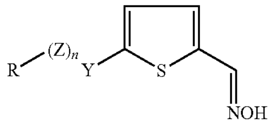

According to a second embodiment, the oxime group is in position 2, X is O and the compound of the invention is a 5-substituted-furan-2-oxime of formula (III), or one of its pharmaceutically acceptable salts:

(III)

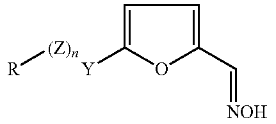

According to said first embodiment, it is preferred that the compound of formula (I) is a 5-substituted-thiophen-2-oxime of formula (II), or one of its pharmaceutically acceptable salts:

(II)

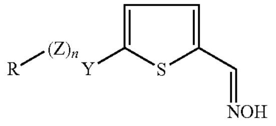

Preferably, Y is —$CH_2$—$CH_2$— or —C≡C—, and n is 0, 1 or 2, preferably n is 0. Preferably, R is a heteroaryl. Preferably said heteroaryl is not substituted. Preferably, said heteroaryl is a pyridine group such as 2-, 3- or 4-pyridino, preferably 3-pyridino.

Preferably, according to said first embodiment, the compounds of formula (II) and their salts are such that:

Y is —$CH_2$—$CH_2$— or —C≡C—, n is 0, 1 or 2, preferably n is 0 or 2; and

R is a heteroaryl, preferably said heteroaryl is not substituted and is a pyridine group such as 2-, 3- or 4-pyridino, preferably 3-pyridino, or R1 and R2 form together with the nitrogen atom a dioxoindolinyl group.

Preferably, the compound of formula (II) or one of its pharmaceutically acceptable salts is chosen from the following compounds: (E/Z)-5-(pyridin-3-ylethynyl)thiophene-2-carbaldehyde oxime 4:

4

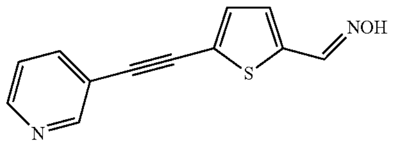

(E/Z)-5-(pyridin-3-ylethynyl)thiophene-2-carbaldehyde oxime hydrochloride NM-27:

NM-27

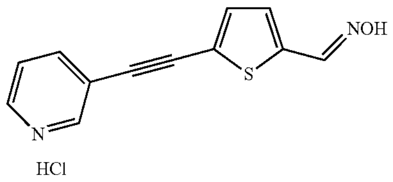

(E/Z)-5-(2-(pyridin-3-yl)ethyl)thiophene-2-carbaldehyde oxime 5:

5

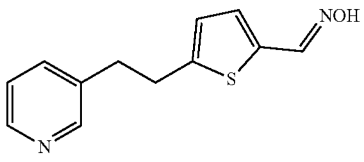

(E/Z)-5-(2-(pyridin-3-yl)ethyl)thiophene-2-carbaldehyde oxime hydrochloride NM-29:

NM-29

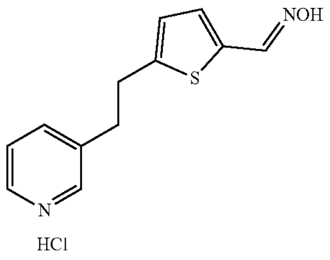

and (Z/E)-5-(4-(1,3-dioxoisoindolin-2-yl)but-1-yn-1-yl)thiophene-2-carbaldehyde oxime CV-65:

CV-65

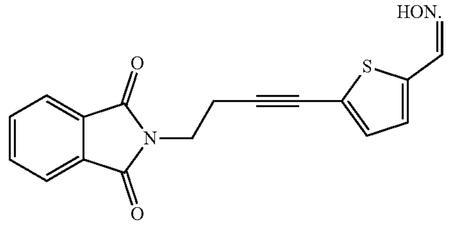

According to said second embodiment, it is preferred that the compound of the invention is a 5-substituted-furan-2-oxime of formula (III), or one of its pharmaceutically acceptable salts:

(III)

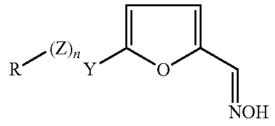

Preferably, Y is $-CH_2-CH_2-$ or $-C\equiv C-$, and n is 0, 1 or 2, preferably n is 0 or 2.

Preferably, R is a heteroaryl or a group —N(R1)(R2). Preferably said heteroaryl is not substituted. Preferably, said heteroaryl is a pyridine group such as 2-, 3- or 4-pyridino, preferably 3-pyridino. Alternatively, preferably R is a substituted heteroaryl, and is an imidazolyl group, preferably 5-imidazolyl, which is preferably substituted by an alkyl group, preferably methyl, or is a 3-oxetanyl group, preferably substituted by a hydroxyl group (—OH). Preferably when R is a group —N(R1)(R2), then R1 is H, and R2 is a heteroaryl, preferably a quinoline group such as a 4-quinolinyl, or a group

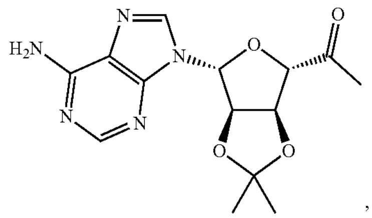 [SMILES: CC(=O)[C@H]1O[C@@H](n2cnc3c(N)ncnc32)[C@@H]2OC(C)(C)O[C@@H]21]

, or R1 and R2 form together with the nitrogen atom a dioxoindolinyl group.

Preferably, according to said second embodiment, the compounds of formula (III) and their salts are such that:

Y is $-CH_2-CH_2-$ or $-C\equiv C-$, n is 0, 1 or 2, preferably n is 0 or 2; and R is a heteroaryl or a group —N(R1)(R2), preferably R is a pyridine group such as 2-, 3- or 4-pyridino, preferably 3-pyridino, a 5-imidazolyl substituted by an alkyl group preferably methyl or a 3-oxetanyl group preferably substituted by a hydroxyl group, or preferably R is a group —N(R1)(R2), wherein R1 is H, and R2 is a heteroaryl, preferably a quinoline group such as a 4-quinolinyl, or a group

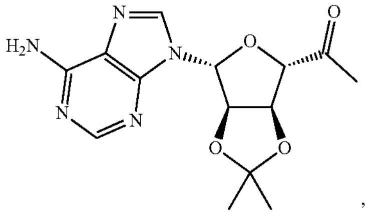 [SMILES: CC(=O)[C@H]1O[C@@H](n2cnc3c(N)ncnc32)[C@@H]2OC(C)(C)O[C@@H]21]

, or R1 and R2 form together with the nitrogen atom a dioxoindolinyl group.

Preferably, the compound of formula (III) or one of its pharmaceutically acceptable salts is chosen from the following compounds:

(E/Z)-5-(pyridin-3-ylethynyl)furan-2-carbaldehyde oxime 8:

8

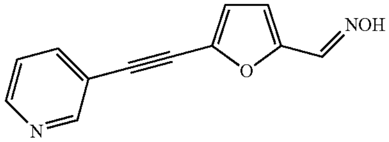

(E/Z)-5-(2-(pyridin-3-yl)ethynyl)furan-2-carbaldehyde oxime hydrochloride NM-28:

NM-28

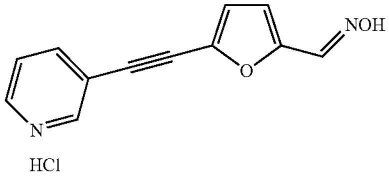

(E/Z)-5-(2-(pyridin-3-yl)ethyl)furan-2-carbaldehyde oxime 9:

9

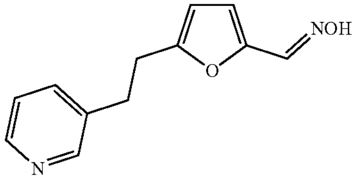

(E/Z)-5-(2-(pyridin-3-yl)ethyl)furan-2-carbaldehyde oxime hydrochloride NM-34:

NM-34

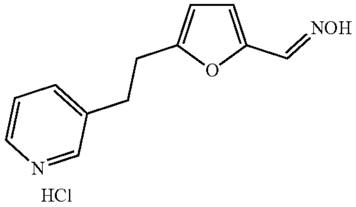

(E/Z)-5-(4-(quinolin-4-ylamino)but-1-yn-1-yl)furan-2-carbaldehyde oxime 11:

11

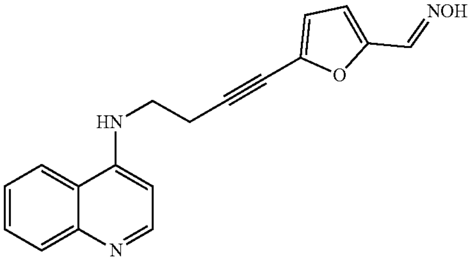

(E/Z)-5-(4-(quinolin-4-ylamino)but-1-yn-1-yl)furan-2-carbaldehyde oxime hydrochloride

NM-53

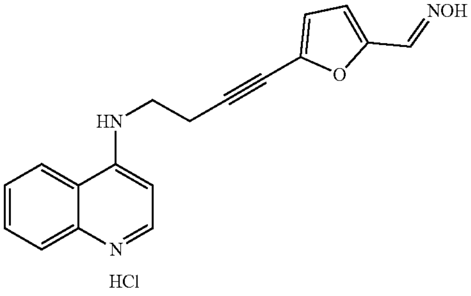

(E/Z)-5-(4-(quinolin-4-ylamino)butyl)furan-2-carbaldehyde oxime 14:

14

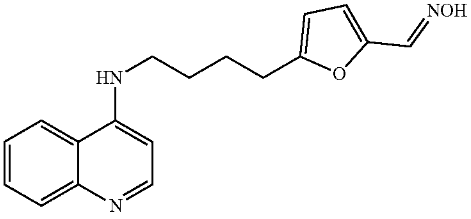

(E/Z)-5-(4-(quinolin-4-ylamino)butyl)furan-2-carbaldehyde oxime hydrochloride NM-80:

NM-80

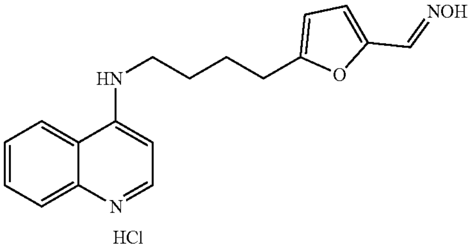

(Z/E)-5-((1-methyl-1H-imidazol-5-yl)ethynyl)furan-2-carbaldehyde oxime 5:

5

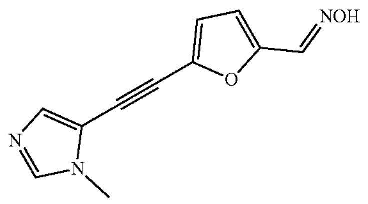

(E/Z)-5-(2-(1-methyl-1H-imidazol-5-yl)ethyl)furan-2-carbaldehyde oxime 6:

6

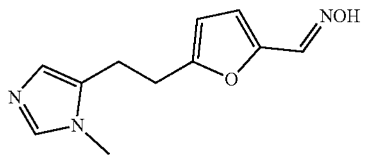

(Z)-5-(2-(1-methyl-1H-imidazol-5-yl)ethyl)furan-2-carbaldehyde oxime hydrochloride FR-152:

FR-152

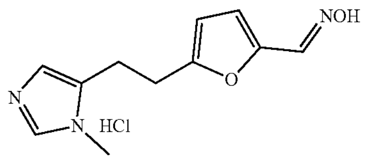

(3aS,4S,6R,6aR)-6-(6-amino-9H-purin-9-yl)-N-(4-(5-((Z)-(hydroxyimino)methyl)furan-2-yl)but-3-yn-1-yl)-2,2-dimethyltetrahydrofuro[3,4-d][1,3]dioxole-4-carboxamide FR-151:

FR-151

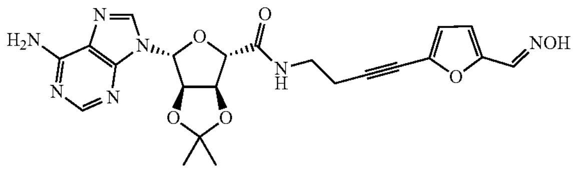

(Z/E)-5-((3-hydroxyoxetan-3-yl)ethynyl)furan-2-carbaldehyde oxime FR-99:

FR-99

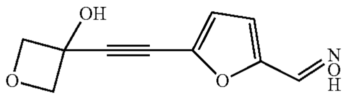

(Z/E)-5-(4-(1,3-dioxoisoindolin-2-yl)but-1-yn-1-yl)furan-2-carbaldehyde oxime CV-59:

CV-59

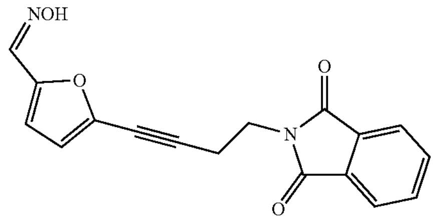

and (Z/E)-5-(4-(1,3-dioxoisoindolin-2-yl)butyl)furan-2-carbaldehyde oxime CV-60

CV60

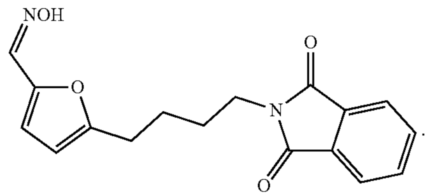

.

Alternatively, according to a last embodiment, preferably, the —Y—(Z)n—R group is in position 4. Preferably, the oxime group is in position 2, X is O and the compound of the invention is a 4-substituted-furan-2-oxime of formula (IV), or one of its pharmaceutically acceptable salts:

(IV)

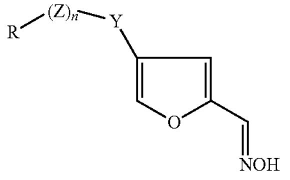

Preferably, Y is —$CH_2$—$CH_2$— or —C≡C—, and n is 0, 1, 2 or 3, preferably n is 0 or 3.

Preferably, R is an aryl or a heteroaryl. Preferably said aryl or said heteroaryl is not substituted. Preferably, said aryl is phenyl. Preferably, said heteroaryl is a pyridine group such as 2-, 3- or 4-pyridino, preferably 3-pyridino.

Preferably, according to said last embodiment, the compounds of formula (IV) and their salts are such that:

Y is —$CH_2$—$CH_2$— or —C≡C—, n is 0, 1, 2 or 3, preferably n is 0 or 3; and

R is an aryl or a heteroaryl, preferably said aryl or said heteroaryl is not substituted and is a phenyl or a pyridine group such as 2-, 3- or 4-pyridino, preferably 3-pyridino.

Preferably, the compound of formula (IV) or one of its pharmaceutically acceptable salts is chosen from the following compounds:

(E/Z)-4-(pyridin-3-ylethynyl)furan-2-carbaldehyde oxime 3

3

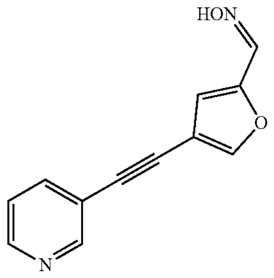

(E/Z)-4-(2-(pyridin-3-yl)ethyl)furan-2-carbaldehyde oxime FR-82:

FR-82

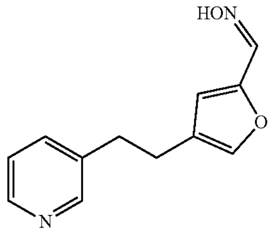

(Z/E)-4-(5-phenylpent-1-yn-1-yl)furan-2-carbaldehyde oxime FR-66:

FR-66

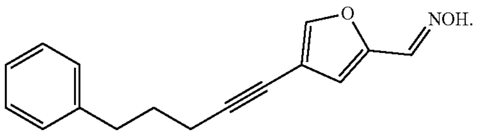

Preferably, the compound of formula (I) or one of its pharmaceutically acceptable salts is chosen from compounds of formula (II), (III) and (IV) and their pharmaceutically acceptable salts.

More preferably, the compound of formula (I) or one of its pharmaceutically acceptable salts is chosen from:

(E/Z)-5-(pyridin-3-ylethynyl)thiophene-2-carbaldehyde oxime 4:

4

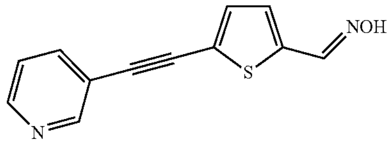

(E/Z)-5-(pyridin-3-ylethynyl)thiophene-2-carbaldehyde oxime hydrochloride NM-27:

NM-27

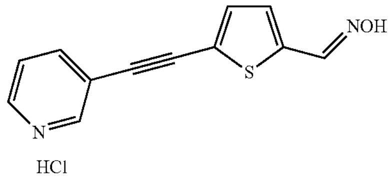

(E/Z)-5-(2-(pyridin-3-yl)ethyl)thiophene-2-carbaldehyde oxime 5:

5

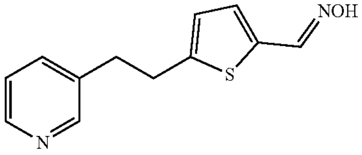

(E/Z)-5-(2-(pyridin-3-yl)ethyl)thiophene-2-carbaldehyde oxime hydrochloride NM-29:

NM-29

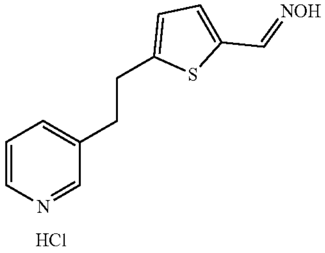

(E/Z)-5-(pyridin-3-ylethynyl)furan-2-carbaldehyde oxime 8:

8

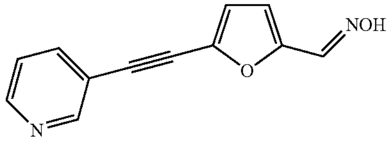

(E/Z)-5-(2-(pyridin-3-yl)ethynyl)furan-2-carbaldehyde oxime hydrochloride NM-28:

NM-28

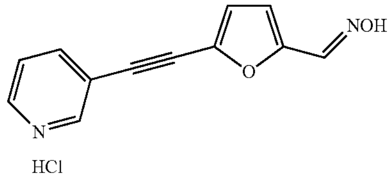

(E/Z)-5-(2-(pyridin-3-yl)ethyl)furan-2-carbaldehyde oxime 9:

9

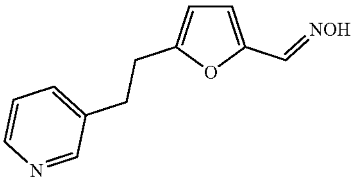

(E/Z)-5-(2-(pyridin-3-yl)ethyl)furan-2-carbaldehyde oxime hydrochloride NM-34:

NM-34

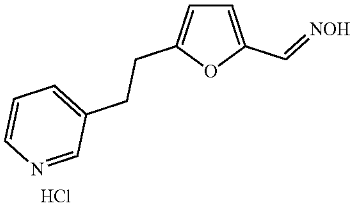

(E/Z)-5-(4-(quinolin-4-ylamino)but-1-yn-1-yl)furan-2-carbaldehyde oxime 11:

11

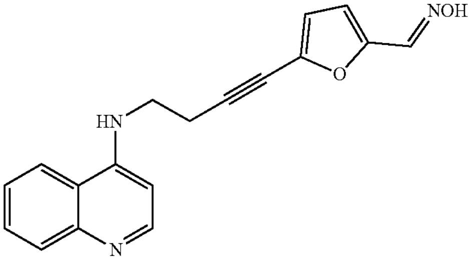

(E/Z)-5-(4-(quinolin-4-ylamino)but-1-yn-1-yl)furan-2-carbaldehyde oxime hydrochloride NM-53:

NM-53

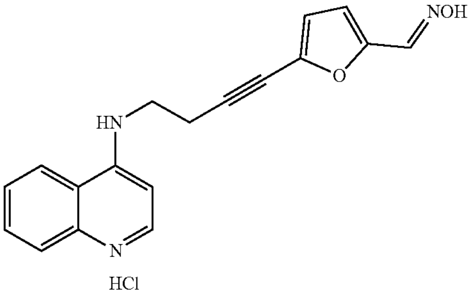

(E/Z)-5-(4-(quinolin-4-ylamino)butyl)furan-2-carbaldehyde oxime 14:

14

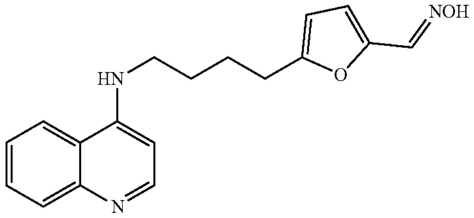

(E/Z)-5-(4-(quinolin-4-ylamino)butyl)furan-2-carbaldehyde oxime hydrochloride NM-80:

NM-80

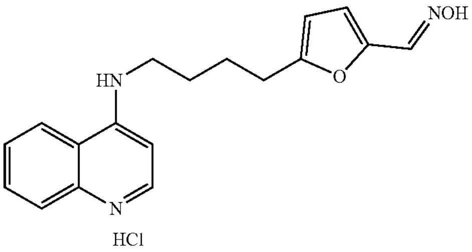

(Z/E)-5-(4-(1,3-dioxoisoindolin-2-yl)but-1-yn-1-yl)thiophene-2-carbaldehyde oxime CV-65:

CV-65

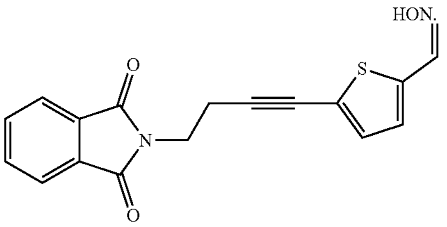

(Z/E)-5-((1-methyl-1H-imidazol-5-yl)ethynyl)furan-2-carbaldehyde oxime 5:

5

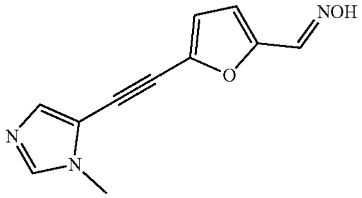

(E/Z)-5-(2-(1-methyl-1H-imidazol-5-yl)ethyl)furan-2-carbaldehyde oxime 6:

6

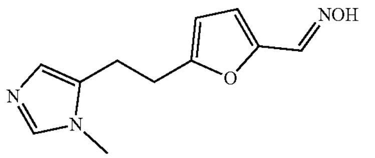

(Z)-5-(2-(1-methyl-1H-imidazol-5-yl)ethyl)furan-2-carbaldehyde oxime hydrochloride FR-152:

FR-152

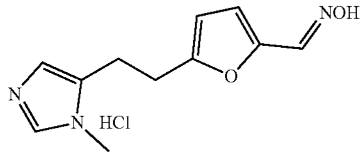

(3aS,4S,6R,6aR)-6-(6-amino-9H-purin-9-yl)-N-(4-(5-((Z)-(hydroxyimino)methyl)furan-2-yl)but-3-yn-1-yl)-2,2-dimethyltetrahydrofuro[3,4-d][1,3]dioxole-4-carboxamide FR-151:

FR-151

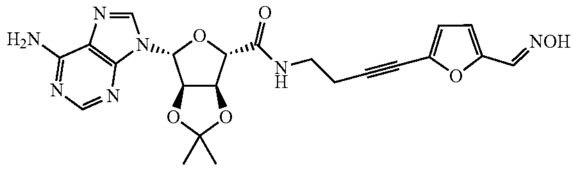

(Z/E)-5-((3-hydroxyoxetan-3-yl)ethynyl)furan-2-carbaldehyde oxime FR-99:

FR-99

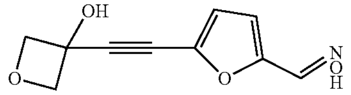

(Z/E)-5-(4-(1,3-dioxoisoindolin-2-yl)but-1-yn-1-yl)furan-2-carbaldehyde oxime CV-59:

CV-59

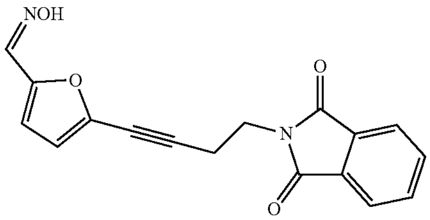

(Z/E)-5-(4-(1,3-dioxoisoindolin-2-yl)butyl)furan-2-carbaldehyde oxime CV-60

CV60

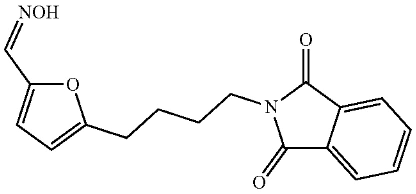

(E/Z)-4-(pyridin-3-ylethynyl)furan-2-carbaldehyde oxime 3

3

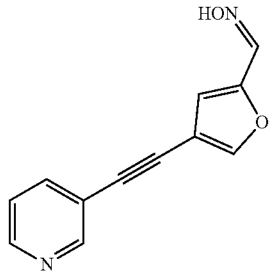

(E/Z)-4-(2-(pyridin-3-yl)ethyl)furan-2-carbaldehyde oxime FR-82:

FR-82

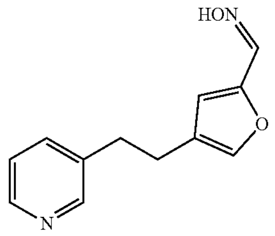

(Z/E)-4-(5-phenylpent-1-yn-1-yl)furan-2-carbaldehyde oxime FR-66:

FR-66

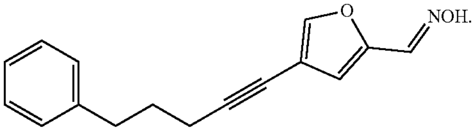

More preferably, the compound of formula (I) or one of its pharmaceutically acceptable salts is such that:

the —Y—(Z)n—R group is in position 5 and the oxime group is in position 2;

X is S or 0;

Y is $-CH_2-CH_2-$ or —C≡C—, n is 0, 1 or 2, preferably n is 0 or 2; and

R is a heteroaryl, preferably a pyridine group such as 2-, 3- or 4-pyridino, preferably 3-pyridino.

Preparation of the Compounds of Formula (I)

A compound of formula (I) according to the invention may be synthesized by any appropriate method. For example, when n is 0, the compounds of formula (I) may be prepared according to the following scheme:

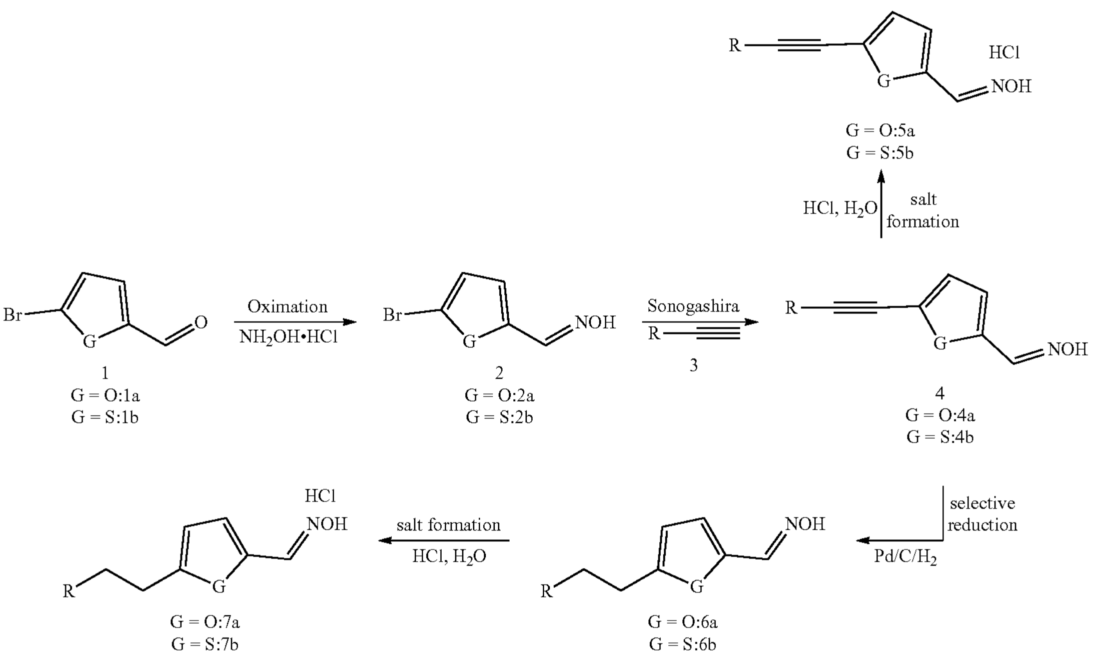

In the above scheme, G is X.

Such methods and others are exemplified in the following examples.

Preferably, the compounds of formula (I) are synthetized as described below. Such a process is chemoselective. Particularly, it does not necessitate any previous protection step of the oxime. Said process comprises a minimal number of steps (one or two), is quickly performed, at ambient temperature.

The main steps are as follows: As shown in the above scheme, commercially available bromo-aldehyde 1 is first converted to the oxime upon treatment with hydroxylamine hydrochloride affording 2.

Subsequent late stage Sonogashira cross-coupling of 2 with alkyne 3, yield the unsaturated reactivator 4 (which is of formula (I)). Selective atmospheric pressure hydrogenation of the triple bond of 4 under Pd/C catalysis with hydrogen, afford reactivator 6 (which is of formula (I)), that can be converted to the hydrochloric salt, after reaction with aqueous HCl leading to compounds of formula (II) 7. 4 is converted to hydrochloride upon treatment with aqueous HCl to yield 5 (which is of formula (I)).

Compounds 4 to 7 are all according to the invention.

When n is 1, 2 or 3, then the above process is also applicable.

Thus, the present invention also relates to a process for preparing a compound of formula (I), which comprises the following steps:

- a Sonogashira coupling reaction between a terminal alkyne

and an isomer of unprotected bromo-thiophenoxime or an isomer of unprotected bromo-furanoxime, preferably under palladium catalysis, to obtain the conjugate

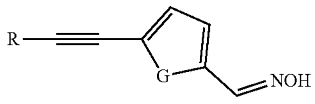

(which is of formula (I); G is X);

- optionally, said conjugate is then submitted to hydrogenation, preferably with Pd/C catalyst in heterogeneous conditions, to provide the corresponding alkene, and finally the hybrid reactivator

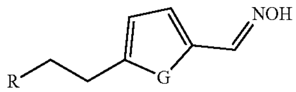

(which is of formula (I); G is X).

Pharmaceutical Uses of the Compounds of the Invention

The compounds of this invention may be used in the treatment of a nervous and/or respiratory failure due to intoxication with at least one organophosphorous nerve agent which may preferably be selected from warfare agents such as O-ethyl S-[2-(diisopropylamino)ethyl]methylphosphonothioate (VX), tabun, sarin, cyclosarin and soman and pesticides such as paraoxon, parathion and tetraethyl pyrophosphate (TEPP). The compounds of the invention may be used in the treatment of a nervous and/or respiratory failure due to intoxication with at least one organophosphorous nerve agent, by virtue of their reactivation potency of organophosphorous inhibited cholinesterases, including acetylcholinesterase and butyrylcholinesterase. These compounds may alternatively be used in the treatment of diseases, which involve a reduced production of acetylcholine that may be overcome by the administration of acetylcholinesterase inhibitors. Examples of such diseases include in particular neurological diseases such as Alzheimer's disease.

These compounds may alternatively be used in the treatment of cancer, thanks to their action as inhibitors of histone deacetylases (HDAC).

The compound of this invention is usually included in a pharmaceutical composition comprising at least one compound according to the invention and a pharmaceutically acceptable support.

The amount of compound of formula (I) in the composition according to the invention may vary in a broad range depending upon the patient, the mode of administration and the expected effect.

The compound or composition according to the invention can be administered orally or non-orally, for instance via topical, parenteral, intramuscular, intravenous, cutaneous, nasal or rectal route.

The pharmaceutical composition of the invention can present different forms including granules, powders, tablets, capsules, syrups, emulsions, suspensions, and forms used for non-oral administration, for instance injections, sprays, transdermal patches or suppositories. These pharmaceutical forms can be prepared via known conventional techniques.

The preparation of an orally administered solid pharmaceutical form can be for instance performed by the following process: an excipient (for example lactose, sucrose, starch or mannitol), a desintegrant (for example calcium carbonate, calcium carboxymethylcellulose, alginic acid, sodium carboxymethylcellulose, colloidal silicon dioxide, sodium croscarmellose, crospovidone, guar gum, magnesium aluminium silicate, microcrystalline cellulose, cellulose powder, pregelatinised starch, sodium alginate or starch glycolate), a binder (for example alpha-starch, gum arabic, carboxymethylcellulose, polyvinylpyrrolidone, hydroxypropylcellulose, alginic acid, carbomer, dextrin, ethylcellulose, sodium alginate, maltodextrin, liquid glucose, magnesium aluminium silicate, hydroxyethylcellulose, methylcellulose or guar gum) and a lubricant (for example talc, magnesium stearate or polyethylene 6000) are added to the active principle and the mixture obtained is then tabletted. If necessary, the tablet can be coated via the known techniques, in order to mask the taste (for example with cocoa powder, mint, borneol or cinnamon powder) or to allow enteric dissolution or sustained release of the active principles. Coating products that can be used are, for example, ethylcellulose, hydroxymethylcellulose, polyoxyethylene glycol, cellulose acetophthalate, hydroxypropylmethylcellulose phthalate and Eudragit® (methacrylic acid-acrylic acid copolymer), Opadry® (hydroxypropylmethylcellulose+macrogol+titanium oxide+lactose monohydrate). Pharmaceutically acceptable colorants may be added (for example yellow iron oxide, red iron oxide or quinoline yellow lake).

Liquid pharmaceutical forms for oral administration include solutions, suspensions and emulsions. The aqueous solutions can be obtained by dissolving the active principle in water, followed by addition of flavourings, colorants, stabilisers and/or thickeners, if necessary. In order to improve the solubility, it is possible to add ethanol, propylene glycol or any other pharmaceutically acceptable non-aqueous solvent. The aqueous suspensions for oral use can be obtained by dispersing the finely divided active principle in water with a viscous product, such as a natural or synthetic gum or resin, methylcellulose or sodium carboxymethylcellulose.

The pharmaceutical forms for injection can be obtained, for example, by the following process. The active principle is dissolved, suspended or emulsified either in an aqueous medium (for example distilled water, physiological saline or Ringer's solution) or in an oily medium (for example olive oil, sesame seed oil, cottonseed oil, corn oil or propylene glycol), with a dispersant (for example Tween® 80, HCO® 60 (Nikko Chemicals), polyethylene glycol, carboxymethylcellulose or sodium alginate), a preserving agent (for example methyl p-hydroxybenzoate, propyl p-hydroxybenzoate, benzyl alcohol, chlorobutanol or phenol), an isotonicity agent (for example sodium chloride, glycerol, sorbitol or glucose) and optionally other additives, such as, if desired, a solubilizing agent (for example sodium salicylate or sodium acetate) or a stabilizer (for example human serum albumin).

Pharmaceutical forms for external use (topical use) can be obtained from a solid, semi-solid or liquid composition containing the active principle. For example, to obtain a solid form, the active principle can be treated with excipients (for example lactose, mannitol, starch, microcrystalline cellulose or sucrose) and a thickener (for example natural gums, cellulose derivatives or acrylic polymers) so as to convert them into powder. The liquid pharmaceutical compositions are prepared in substantially the same way as the forms for injection, as indicated previously. The semi-solid pharmaceutical forms are preferably in the form of aqueous or oily gels or in the form of pomades. These compositions may optionally contain a pH regulator (for example carbonic acid, phosphoric acid, citric acid, hydrochloric acid or sodium hydroxide) and a preserving agent (for example a p-hydroxybenzoic acid ester, chlorobutanol or benzalkonium chloride).

A method for the treatment of a nervous and/or respiratory failure due to intoxication with at least one organophosphorous nerve agent, comprising administering at least one compound according to the invention is also described herein.

A method for the treatment of a neurological disease such as Alzheimer's disease, comprising administering at least one compound according to the invention is also described herein.

A method for the treatment of a cancer, comprising administering at least one compound according to the invention is also described herein.

A method for the treatment of a virus, comprising administering at least one compound according to the invention is also described herein.

Within the context of the invention, the term treatment denotes curative, symptomatic, and/or preventive treatments. In particular, it can refer to reducing the progression of the disease, reducing or suppressing at least one of its symptoms or complications, or improving in any way the state of health of patients.

The administration of the compounds or of the composition according to the invention may be performed before, during or after the exposition of the subject to the organophosphorous nerve agent.

In the present invention, the terms "subject" and "patient" are used indifferently and designate a human subject.

The amount of compound according to the invention to be administered according to the invention may vary in a broad range depending upon the patient, the mode of administration and the expected effect. In particular, the amount of compound according to the invention may be comprised between 200 mg and 4000 mg, with up to 3 daily intakes.

The compound or composition according to the invention may be co-administered with at least one other active agent, such as an antimuscarinic agent, in particular atropine, an anticonvulsant, in particular diazepam or one of its prodrugs, such as avizafone, and/or a bioscavenger able to capture and/or degrade OPNAs in blood, such as human butyrylcholinesterase.

The term co-administered means that the administration of the compound or composition according to the invention and that of the other active agent can be simultaneous, sequential and/or separate.

Other Uses of the Compounds of the Invention

The compounds of this invention may further be used as tools for in vivo and/or in vitro biological studies. In this application, the compounds according to the invention may include one or more isotopes, which will allow for their detection.

The following examples are provided as illustrative, and not limitative, of the present invention.

EXAMPLES

Example 1: Synthesis of Compounds of the Invention

General Methods

All starting materials and reagents were purchased from commercial sources and used as received without further purification. Air and $H_2O$ sensitive reactions were performed in flame-dried glassware under Ar atmosphere. Moisture sensitive reagents were introduced via a dry syringe. Anhydrous solvents were supplied over molecular sieves, and used as received. Petroleum ether (PE) refers to the 40-60° C. boiling fraction. Reactions were monitored by thin-layer chromatography (TLC) with silica gel 60 $F_{254}$ 0.25 mm pre-coated glass plates. Compounds were visualized by using $UV_{254}$ and/or phosphomolybdic acid stain [3 g $12MoO_3 \cdot H_3PO_4.xH_2O$ in 100 mL EtOH] followed by heating with a heat gun. Flash column chromatography was performed using Macherey-Nagel silica gel 60 (15-40 μm). NMR experiments were recorded with a Bruker Avance 400 spectrometer at 400 MHz for $^1H$ nuclei and at 100 MHz for $^{13}C$ nuclei. The chemical shifts are expressed in part per million (ppm) relative to TMS (δ=0 ppm) and the coupling constant J in Hertz (Hz). NMR multiplicities are reported using the following abbreviations: br=broad, s=singlet, d=doublet, t=triplet, q=quadruplet, m=multiplet. HRMS were recorded on a Bruker microTOF spectrometer.

Experimental Procedures (E/Z)-5-(pyridin-3-ylethynyl)thiophene-2-carbaldehyde oxime hydrochloride NM-27

(E/Z)-5-(2-(pyridin-3-yl)ethyl)thiophene-2-carbaldehyde oxime hydrochloride NM-29

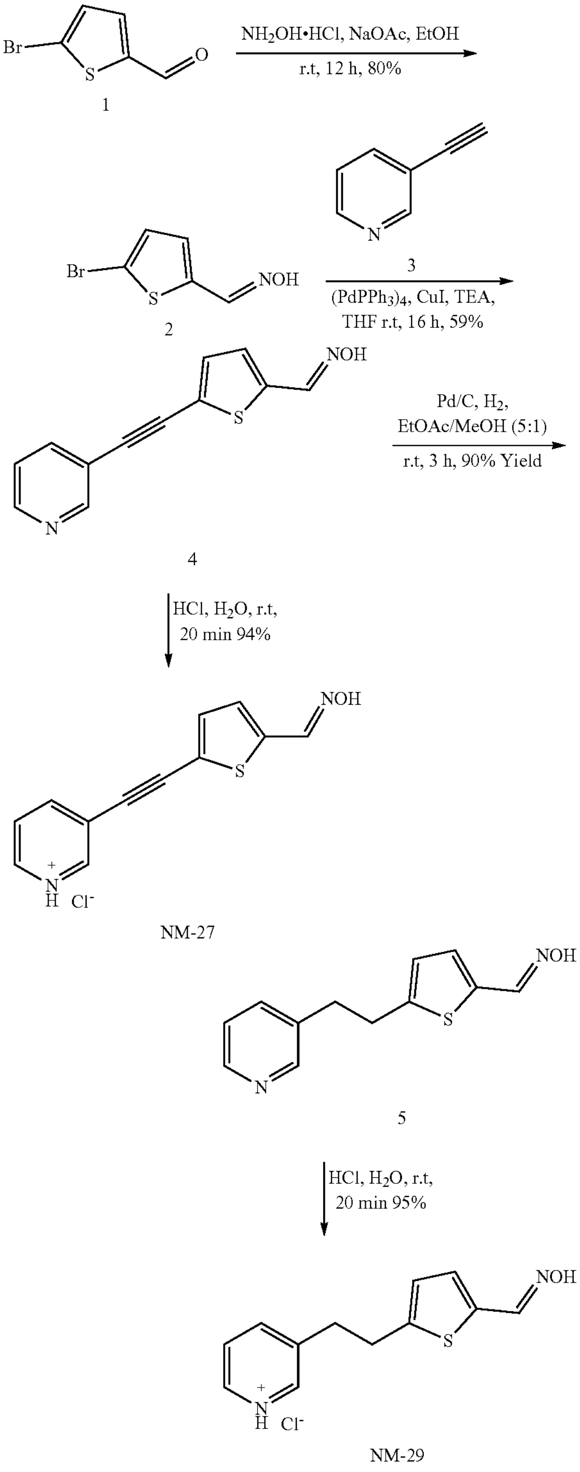

(E)-5-bromothiophene-2-carbaldehyde oxime 2

2

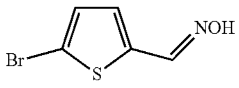

A solution of commercially available 5-bromothiophene-2-carbaldehyde 1 (1 g, 5.23 mmol, 1 equiv), hydroxylamine hydrochloride (727 mg, 10.46 mmol, 2 equiv), and $CH_3CO_2Na$ (1.28 g, 15.70 mmol, 3 equiv) in dry ethanol (10 mL) was stirred at room temperature for 16 h. Upon completion, the reaction mixture was filtered through a small celite pad. The filtrate was concentrated under reduced pressure and the residue was purified by column chromatography (EtOAc/PE 1:9) to afford pure (E)-5-bromothiophene-2-carbaldehyde oxime 2 as a white solid (850 mg, 79.4%); $R_f$ (10% EtOAc/PE) 0.3; $^1H$ NMR (400 MHz, $CDCl_3$): δ 9.45 (brs, 1H, OH), 7.63 (s, 1H), 7.12 (d, J=4.0 Hz, 1H), 7.07 (d, J=4.0 Hz, 1H).

(E/Z)-5-(pyridin-3-yethynyl)thiophne-2-carbaidehyde oxime 4

4

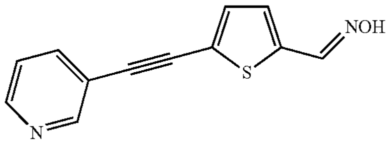

To a degassed solution of (E)-5-bromothiophene-2-carbaldehyde oxime 2 (110 mg, 0.533 mmol, 1.1 equiv) in THF/$Et_3N$ (6 mL/2 mL), $Pd[PPh_3]_4$ (84.2 mg, 0.072 mmol, 0.15 equiv) and CuI (27.7 mg, 0.145 mmol, 0.3 equiv) were added. After degassing the reaction mixture for 5 min at room temperature, 3-ethynylpyridine 3 (50 mg, 0.485 mmol, 1 equiv) was added dropwise and the reaction mixture was stirred at the room temperature for 16 h. Upon completion, the reaction mixture was concentrated under reduced pressure and the residue was purified by column chromatography (EtOAc/PE, 1:1) to afford (E)-5-(pyridin-3-ylethynyl) thiophene-2-carbaldehyde oximeas a white solid (65 mg, 58.7%); $R_f$(50% EtOAc/PE) 0.25; IR(neat): $v_{max}$3058, 2790, 1493, 1229, 1193, 1049, 924, 797, 698, 567 $cm^{-1}$; HRMS ($ESI^+$): m/z calcd for $C_{12}H_8N_2OS^+$ 229.0430 found 229.0433. $^1H$ NMR (400 MHz, DMSO-$d_6$): δ ppm 12.32 (s, 1H), 8.76 (s, 1H), 8.60 (d, J=3.8 Hz, 1H), 7.99 (d, J=7.9 Hz, 1H), 7.93 (s, 1H), 7.47 (bs, 3H); $^{13}C$ NMR (101 MHz, DMSO-$d_6$): δ ppm 151.41, 149.25, 139.56, 138.40, 132.59, 132.18, 131.22, 124.93, 123.66, 118.94, 91.72, 85.62.

(E/Z)-5-(pyridin-3-ylethynyl)thiophene-2-carbaldehyde oxime hydrochloride NM-27

NM-27

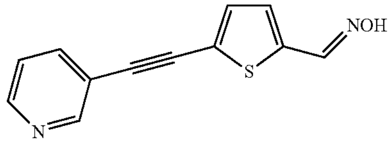

HCl

To a solution of (E)-5-(pyridin-3-ylethynyl)thiophene-2-carbaldehyde oxime 4 (20 mg, 0.087 mmol) in water (3 ml) was added 2N HCl (1 mL) at room temperature and stirred for 20 min at same temperature. Upon completion, solvent was distilled off under reduced pressure and the resulting solid was washed with diethyl ether (2×3 mL). The solid was dried under vacuum to give cis-trans isomers (1:0.2 ratio) of (E/Z) 5-(pyridin-3-ylethynyl)thiophene-2-carbaldehyde oxime hydrochloride NM-27 as a pale yellow solid (21.5 mg, 93.4%); IR(neat): $v_{max}$ 3051, 2924, 2585, 2358, 2216, 1442, 1425, 1254, 985, 798, 672, 546 $cm^{-1}$; $^1H$ NMR (400 MHz, $CD_3OD$): δ ppm 9.12 (bs, 1.2H), 8.86 (bs, 1.2H), 8.78-8.69 (m, 1.2H), 8.24 (s, 0.2H), 8.14 (s, 1.2H), 7.81 (s, 1H), 7.48 (d, J=3.9 Hz, 1H), 7.41 (d, J=3.7 Hz, 1H), 7.21 (d, J=3.7 Hz, 0.2H), 7.09 (d, J=3.6 Hz, 0.2H); $^{13}C$ NMR (101 MHz, $CD_3OD$): δ ppm 156.55, 149.25, 144.93, 144.17, 142.48, 141.83, 136.03, 135.71, 134.63, 132.20, 130.04, 128.90, 127.17, 125.75, 121.93, 100.87, 91.49, 91.33, 88.47.

(E/Z)-5-(2-(pyridin-3-yl)ethyl)thiophene-2-carbaldehyde oxime 5

5

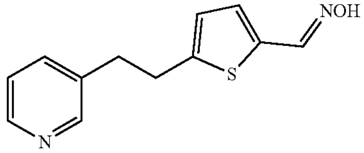

To a solution of (E)-5-(pyridin-3-ylethynyl)thiophene-2-carbaldehyde oxime 4 (25 mg, 0.109 mmol) in 4:1 ratio of EtOAc/MeOH (5 mL) was added 10% Pd/C (10 mg) at room temperature under Argon atmosphere and stirred the mixture for 3 h. Upon completion, the mixture was filtered using small celite pad and concentrated under reduced pressure. The crude was purified by column chromatography (EtOAc/PE, 60:40) to afford cis-trans isomers (1:0.1) of (E/Z)-5-(2-(pyridin-3-yl)ethyl)thiophene-2-carbaldehyde oxime 5 as a white solid (23 mg, 90%); $R_f$(50% EtOA/PE) 0.20; IR (neat): $v_{max}$ 2921, 2851, 2719, 1474, 1429, 1042, 917, 794, 707, 640, 591, 569 $cm^{-1}$; HRMS ($ESI^+$): m/z calcd for $C_{12}H_{13}N_2OS^+$ 233.0769 found 233.0743; $^1H$ NMR (400 MHz, $CDCl_3$): δ ppm 8.48 (bs, 2H), 7.64 (s, 1H), 7.49 (d, J=7.8 Hz, 1H), 7.23 (dd, J=7.4, 5.0 Hz, 1H), 7.18 (d, J=3.7 Hz, 1H), 6.72 (d, J=3.6 Hz, 1H), 3.17 (t, J=7.6 Hz, 2H), 3.02 (t, J=7.6 Hz, 2H); $^{13}C$ NMR (101 MHz, $CDCl_3$): δ ppm 149.56, 149.41, 147.44, 144.76, 136.25, 131.45, 129.37, 125.13, 124.30, 123.49, 34.59, 31.26.

(E/Z)-5-(2-(pyridin-3-yl)ethyl)thiophene-2-carbaldehyde oxime hydrochloride NM-29

NM-29

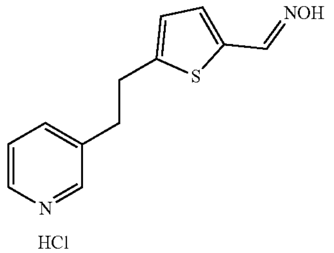

To a solution of (E/Z)-5-(2-(pyridin-3-yl)ethyl)thiophene-2-carbaldehyde oxime 5 (20 mg, 0.087 mmol) in water (3 ml) was added 2N HCl (1 mL) at room temperature and stirred for 20 min at same temperature. Upon completion, solvent was distilled off under reduced pressure and the resulting solid was washed with diethyl ether (2×5 mL). The solid was dried under vacuum to give cis-trans isomers (75:25 ratio) of (E/Z)-5-(2-(pyridin-3-yl)ethyl)thiophene-2-carbaldehyde oxime hydrochloride NM-29 as a white solid (22 mg, 95% yield); IR(neat): $v_{max}$ 3050, 2924, 2359, 2340, 1526, 1254, 1008, 987, 804, 674, 547 $cm^{-1}$; HRMS ($ESI^+$): m/z calcd for $C_{12}H_{13}N_2OS^+$ 233.0744 found 233.0743; $^1H$ NMR (400 MHz, $CD_3OD$): δ ppm 9.06-8.42 (m, 3H), 8.25-7.87 (m, 2H), 7.69-7.37 (s, 0.75H), 7.18-6.89 (bs, 1H), 6.84-6.65 (s, 0.25H), 3.60-3.05 (m, 4H); $^{13}C$ NMR (101 MHz, $CD_3OD$): δ ppm 153.64, 148.90, 148.79, 145.08, 144.89, 142.98, 142.89, 142.81, 142.75, 141.10, 140.97, 137.13, 136.36, 130.39, 128.83, 128.71, 127.56, 127.28, 35.34, 31.76, 31.72.

(E/Z)-5-(2-(pyridin-3-yl)ethynyl)furan-2-carbaldehyde oxime hydrochloride NM-28

(E/Z)-5-(2-(pyridin-3-yl)ethyl)furan-2-carbaldehyde oxime hydrochloride NM-34

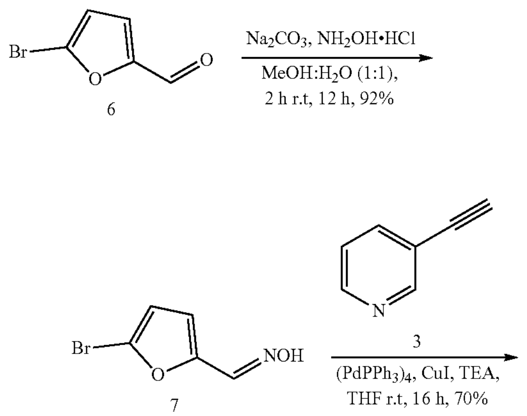

6

7

3

-continued

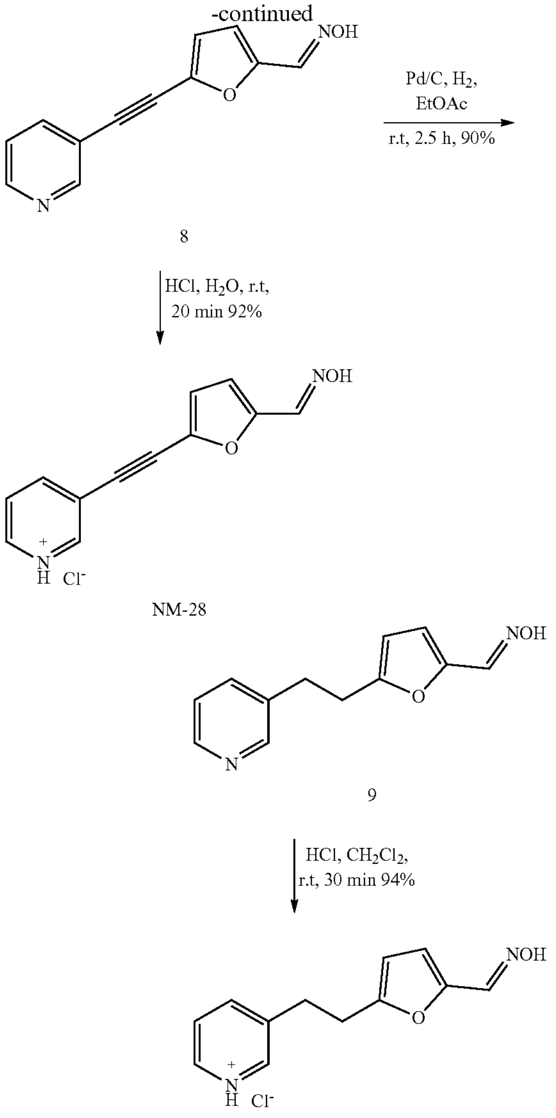

8

NM-28

9

NM-34

(E/Z)-5-bromofuran-2-carbaldehyde oxime 7

7

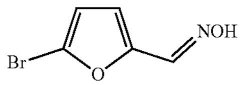

A solution of commercially available 5-bromofuran-2-carbaldehyde 6 (2.5 g, 14.28 mmol, 1 equiv), hydroxylamine hydrochloride (1.98 mg, 28.48 mmol, 2 equiv), and $Na_2CO_3$ (4.54 g, 42.83 mmol, 3 equiv) in 1:1 ratio of $MeOH/H_2O$ (10 mL) was stirred at room temperature for 2 h. Upon completion, the reaction mixture was concentrated, extracted with EtOAc (3×30 mL) dried over anhydrous $Na_2SO_4$ and concentrated by vacuo. The crude was purified by column chromatography (EtOAc/PE 1:9) to afford cis-trans isomers (1:0.55 ratio) of (E/Z)-5-bromofuran-2-carbaldehyde oxime 7 as a white solid (2.5 g, 92.2%); $R_f$ (10% EtOAc/PE) 0.55; $^1H$ NMR (400 MHz, $CDCl_3$): δ ppm 7.92 (s, 0.55H), 7.45 (s, 1H), 7.27 (d, J=3.5 Hz, 1H), 6.58 (d, J=3.4 Hz, 0.55H), 6.47 (dd, J=3.5, 0.5 Hz, 1H), 6.40 (d, J=3.5 Hz, 0.55H).

(E/Z)-5-(pyridin-3-ylethynyl)furan-2-carbaidehyde oxime 8

8

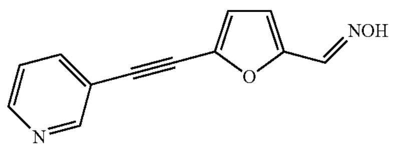

To a degassed solution of (E/Z)-5-bromofuran-2-carbaldehyde oxime 7 (101 mg, 0.531 mmol, 1.1 equiv) in THF/$Et_3N$ (4 mL/2 mL), Pd$[PPh_3]_4$ (84.2 mg, 0.072 mmol, 0.15 equiv) and CuI (27.7 mg, 0.145 mmol, 0.3 equiv) were added. After degassing the reaction mixture for 5 min at room temperature, 3-ethynylpyridine (50 mg, 0.485 mmol, 1 equiv) was added dropwise and the reaction mixture was stirred at the room temperature for 16 h. Upon completion, the reaction mixture was concentrated under reduced pressure and the residue was purified by column chromatography to afford cis-trans isomers (1:0.8 ratio) of (E/Z)-5-(pyridin-3-ylethynyl)furan-2-carbaldehyde oxime 8 as a light yellow solid (72 mg, 70%); IR(neat): $v_{max}$2808, 2360, 1479, 1407, 1019, 986, 955, 791, 695, 518 $cm^{-1}$; $R_f$ (30% EtOAc/PE) 0.30; HRMS ($ESI^+$): m/z calcd for $C_{12}H_9N_2O_2$+ 213.0662 found 213.0658; $^1$H NMR (400 MHz, DMSO-$d_6$): δ ppm 12.13 (s, 0.8H), 11.57 (s, 1H), 8.80 (s, 1.8H), 8.65 (s, 1.8H), 8.06 (s, 1H), 8.05-8.00 (m, 1.8H), 7.61 (s, 0.8H), 7.54-7.46 (m, 1.8H), 7.29 (d, J=3.6 Hz, 0.8H), 7.11 (dd, J=3.6, 0.5 Hz, 0.8H), 7.06 (d, J=3.6 Hz, 1H), 6.84 (d, J=3.6 Hz, 1H); $^{13}$C NMR (101 MHz, DMSO-$d_6$): δ ppm 151.50, 149.67, 149.55, 146.58, 138.53, 135.77, 134.75, 134.73, 132.05, 132.02, 131.53, 131.43, 128.81, 128.70, 118.91, 118.57, 117.59, 112.85, 91.60, 91.49, 82.24, 82.11.

(E/Z)-5-(pyridin-3-ylethynyl)furan-2-carbaldehyde oxime hydrochloride NM-28

NM-28

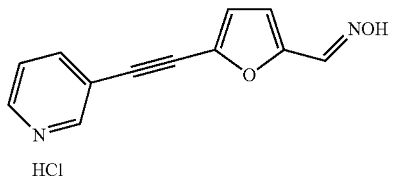

To a solution of (E/Z)-5-(pyridin-3-ylethynyl)furan-2-carbaldehyde oxime 8 (30 mg, 0.141 mmol) in water (3 ml) was added 2N HCl (1 mL) at room temperature and stirred for 30 min at same temperature. Upon completion, solvent was distilled off under reduced pressure and the resulting solid was washed with diethyl ether (2×3 mL). The solid was dried under vacuum to give trans-cis isomers (55:45 ratio) isomers of(E/Z)-5-(pyridin-3-ylethynyl)furan-2-carbaldehyde oxime hydrochloride NM-28 as a white solid (30 mg, 92%); IR (neat): $v_{max}$3104, 3024, 2850, 2215, 1540, 1146, 982, 923, 795, 741, 672, 620 $cm^{-1}$; $^1$H NMR (400 MHz, $CD_3OD$): δ ppm 9.18 (bs, 1H), 8.94 (bs, 1H), 8.82-8.68 (m, 1H), 8.17 (s, 1H), 8.01 (s, 0.45H), 7.48 (s, 0.55H), 7.38 (d, J=3.3 Hz, 0.55H), 7.10 (d, J=3.4 Hz, 0.55H), 7.05 (d, J=3.4 Hz, 0.45H), 6.80 (d, J=3.3 Hz, 0.45H); $^{13}$C NMR (101 MHz, $CD_3OD$): δ ppm 152.16, 149.03, 148.93, 145.14, 144.99, 142.40, 142.35, 142.26, 142.24, 139.83, 136.91, 135.81, 121.67, 121.30, 119.00, 113.49, 88.69, 88.46, 87.41, 87.34.

(E/Z)-5-(2-(pyridin-3-yl)ethyl)furan-2-carbaldehyde oxime 9

9

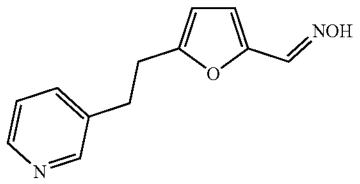

To a solution of (E/Z)-5-(pyridin-3-ylethynyl)furan-2-carbaldehyde oxime 8 (30 mg, 0.141 mmol) in EtOAc (5 mL) was added 10% Pd/C (10 mg) at room temperature under Argon atmosphere and stirred the mixture for 2.5 h under $H_2$ atmosphere using balloon pressure. Upon completion, the mixture was filtered using celite pad and concentrated under reduced pressure. The crude was purified by column chromatography (EtOAc/PE, 40:60) to afford cis-trans isomers (60:40 ratio) of (E/Z)-5-(2-(pyridin-3-yl)ethyl)furan-2-carbaldehyde oxime as white solid (27 mg, 88%); $R_f$ (30% EtOAc/PE) 0.20; IR(neat): $V_{max}$ 2850, 2289, 2161, 1579, 1524, 1460, 1425, 1020, 967, 913, 800, 706, 640 $cm^{-1}$; HRMS ($ESI^+$): m/z calcd for $C_{12}H_{13}N_2O_2^+$ 217.0957 found 217.0971; $^1$H NMR (400 MHz, $CD_3OD$): 5 ppm 8.40-8.27 (m, 2H), 7.90 (s, 0.4H), 7.70-7.61 (m, 1H), 7.37-7.29 (m, 1.6H), 7.14 (d, J=3.3 Hz, 0.6H), 6.51 (d, J=3.3 Hz, 0.40H), 6.15 (dd, J=3.3, 0.5 Hz, 0.6H), 6.08 (d, J=3.3 Hz, 0.40H), 3.06-2.95 (m, 4H); $^{13}$C NMR (101 MHz, $CD_3OD$): δ ppm 157.60, 156.67, 150.10, 150.08, 148.09, 147.82, 147.79, 147.51, 145.99, 140.68, 138.58, 138.56, 138.32, 138.20, 137.10, 125.09, 119.31, 114.06, 109.85, 109.22, 32.08, 32.07, 30.36, 30.26.

(E/Z)-5-(2-(pyridin-3-yl)ethyl)furan-2-carbaldehyde oxime hydrochloride NM-34

NM-34

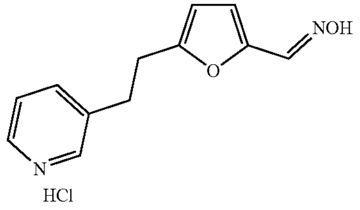

To a solution of (E/Z)-5-(2-(pyridin-3-yl)ethyl)furan-2-carbaldehyde oxime 9 (20 mg, 0.092 mmol) in $CH_2Cl_2$ (3 ml) was added 2N HCl (1 mL) at room temperature and stirred for 30 min at same temperature. Upon completion, solvent was distilled off under reduced pressure and the resulting solid was washed with diethyl ether (2×3 mL). The solid was dried under vacuum to give cis-trans isomers (60:40 ratio) of (E/Z)-5-(2-(pyridin-3-yl)ethyl)furan-2-carbaldehyde oxime hydrochloride NM-34 as a light brown solid (22 mg, 94%); IR (neat): $v_{max}$3155, 3051, 3004, 2627, 2083, 1558, 1520, 1470, 1024, 1011, 807, 682 $cm^{-1}$; $^1H$ NMR (400 MHz, $CD_3OD$): δ ppm 8.86-8.70 (m, 2H), 8.55 (t, J=7.9 Hz, 1H), 8.11-8.00 (m, 1H), 7.99 (s, 0.4H), 7.74 (s, 0.6H), 7.39 (d, J=2.6 Hz, 0.6H), 6.63 (d, J=2.8 Hz, 0.4H), 6.41 (d, J=2.8 Hz, 0.6H), 6.23 (d, J=2.8 Hz, 0.4H), 3.32 (m, 2H), 3.17 (m, 2H); $^{13}C$ NMR (101 MHz, $CD_3OD$): δ ppm 157.38, 155.84, 147.14, 147.12, 146.53, 141.76, 141.59, 141.08, 141.05, 139.41, 139.31, 127.12, 127.06, 121.60, 114.07, 110.20, 108.81, 30.43, 30.24, 28.10, 28.08.

(E/Z)-5-(4-(quinolin-4-ylamino)but-1-yn-1-yl)furan-2-carbaldehyde oxime hydrochloride NM-53

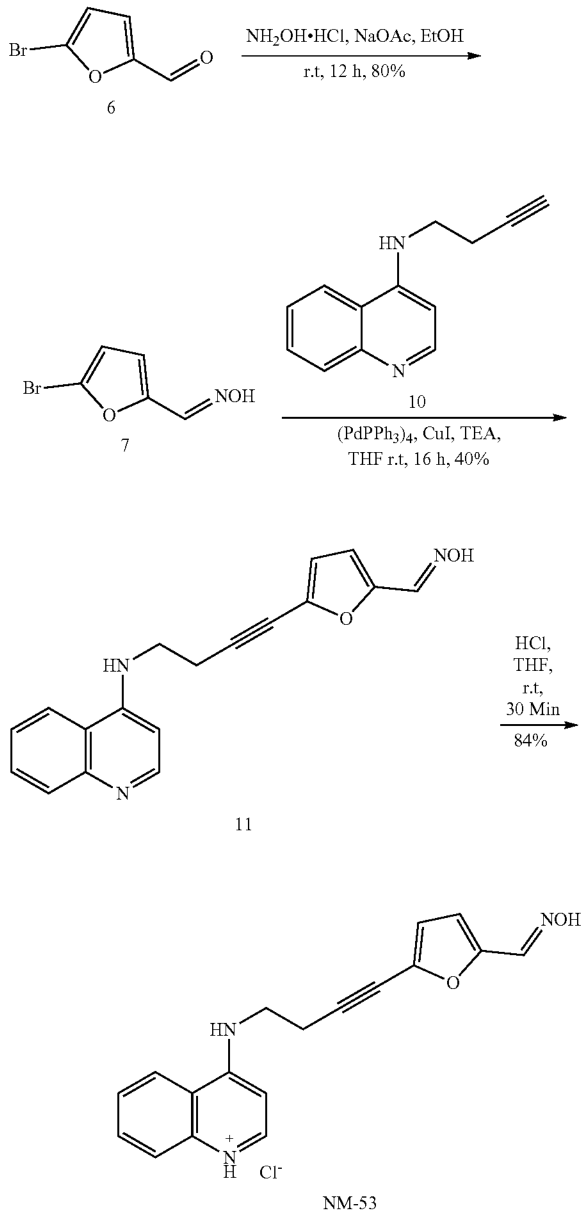

(E/Z)-5-(4-(quinolin-4-ylamino)but-1-yn-1-yl)furan-2-carbaldehyde oxime 11

11

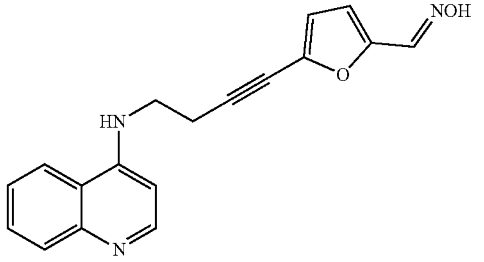

To a degassed solution of (E/Z)-5-bromofuran-2-carbaldehyde oxime 7 (32 mg, 0.168 mmol, 1.1 equiv) in THF/$Et_3N$ (6 mL/2 mL), $Pd[PPh_3]_4$ (26.5 mg, 0.022 mmol, 0.15 equiv) and CuI (8.7 mg, 0.045 mmol, 0.3 equiv) were added. After degassing the reaction mixture for 5 min at room temperature, N-(but-3-yn-1-yl)quinolin-4-amine 10 (30 mg, 0.152 mmol, 1 equiv) was added dropwise and the reaction mixture was stirred at the room temperature for 16 h. Upon completion, the reaction mixture was concentrated under reduced pressure and the residue was purified by column chromatography (100% EtOAc to MeOH/EtOAc 5:95) to afford trans-cis isomers (1:0.5 ratio) of (E/Z)-5-(4-(quinolin-4-ylamino)but-1-yn-1-yl)furan-2-carbaldehyde oxime 11 as an off white solid (18 mg, 36%); $R_f$ (10% MeOH/EtOAc) 0.20; IR(neat): $v_{max}$3050, 2924, 2567, 2357, 1550, 1442, 1172, 1172, 986, 804, 763, 582, 486 $cm^{-1}$; HRMS ($ESI^+$): m/z calcd for $C_{18}H_{16}N_3O_2$ 306.122218 found 306.123703; $^1H$ NMR (400 MHz, DMSO-$d_6$): δ ppm 11.98 (s, 0.67H), 11.42 (s, 0.33H), 8.42 (d, J=5.4 Hz, 1H), 8.20 (d, J=8.5 Hz, 1H), 7.97 (s, 0.33H), 7.79 (d, J=7.7 Hz, 1H), 7.67-7.57 (m, 1H), 7.49 (s, 0.67H), 7.47-7.42 (m, 2H), 7.17 (d, J=3.5 Hz, 0.67H), 6.78 (d, J=3.5 Hz, 0.67H), 6.72 (dd, J=9.0, 3.5 Hz, 0.67H), 6.58 (d, J=5.4 Hz, 1H), 3.58 (dd, J=12.8, 6.8 Hz, 2H), 2.90 (t, J=6.9 Hz, 2H); $^{13}C$ NMR (101 MHz, DMSO-$d_6$): δ ppm 150.38, 149.69, 148.20, 147.88, 145.47, 138.53, 136.83, 135.80, 134.78, 128.98, 128.72, 124.11, 124.09, 121.63, 118.71, 117.35, 117.33, 116.76, 116.37, 112.57, 98.49, 94.67, 71.72, 41.01, 40.96, 21.15, 18.86, 18.85.

(E/Z)-5-(4-(quinolin-4-ylamino)but-1-yn-1-yl)furan-2-carbaldehyde oxime hydrochloride NM-53

NM-53

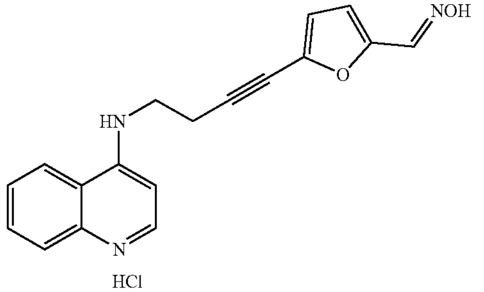

HCl

To a solution of (E/Z)-5-(4-(quinolin-4-ylamino)but-1-yn-1-yl)furan-2-carbaldehyde oxime 11 (8.5 mg, 0.027 mmol) in THF (3 ml) was added 2N HCl (0.1 mL) at room temperature and stirred for 20 min at same temperature. Upon completion, solvent was distilled off under reduced pressure and the resulting solid was washed with diethyl ether. The solid was dried under vacuum to give cis-trans isomers (8:2 ratio) of (E/Z)-5-(4-(quinolin-4-ylamino)but-1-yn-1-yl)furan-2-carbaldehyde oxime hydrochloride NM-53 as a pale yellow solid (8 mg, 84% yield); IR(neat): $v_{max}$3173, 2807, 2220, 1591, 1570, 786, 750 $cm^{-1}$; $^1H$ NMR (400 MHz, $CD_3OD$): δ ppm 8.44-8.41 (m, 2H), 8.01-7.96 (m, 1H), 7.90-7.88 (m, 1.8H), 7.78-7.73 (m, 1H), 7.30 (s, 0.2H), 7.22 (d, J=3.5 Hz, 0.2H), 7.06 (d, J=7.1 Hz, 1H), 6.62 (d, J=3.5 Hz, 0.8H), 6.60 (d, J=3.6 Hz, 0.2H), 6.55 (d, J=3.5 Hz, 0.8H), 3.93 (t, J=6.7 Hz, 2H), 3.07-2.95 (m, 2H); $^1H$ NMR (101 MHz, $CD_3OD$): δ ppm 157.99, 149.77, 143.21, 144.04, 139.35, 139.01, 136.24, 135.03, 135.00, 128.34, 123.75, 121.16, 118.80, 118.37, 117.68, 117.21, 113.35, 99.67, 93.45, 93.29, 73.69, 73.67, 42.97, 42.94, 20.28, 20.21.

(E/Z)-5-(4-(quinolin-4-ylamino)butyl)furan-2-carbaldehyde oxime hydrochloride NM-80

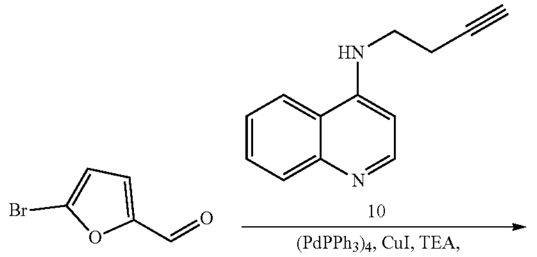

6

10

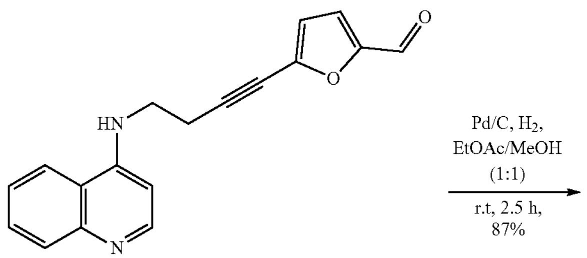

12

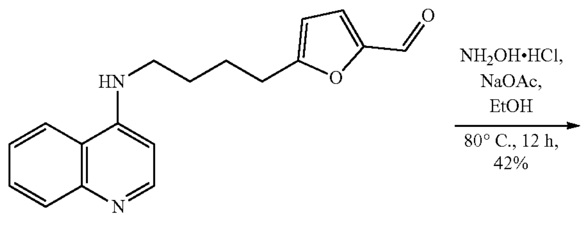

13

-continued

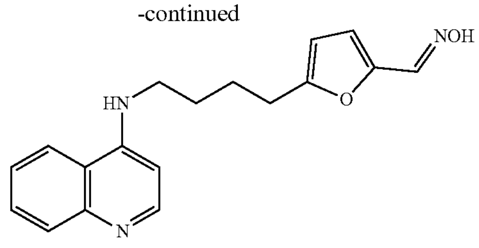

14

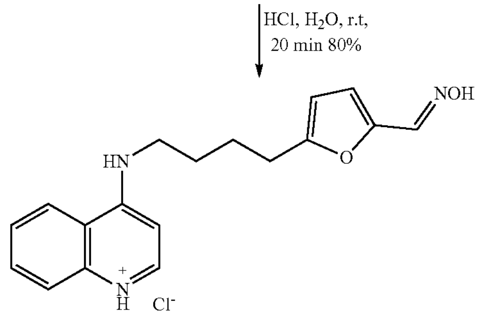

NM-80

5-(4-(quinolin-4-ylamino)but-1-yn-1-yl)furan-2-carbaidehyde 12

12

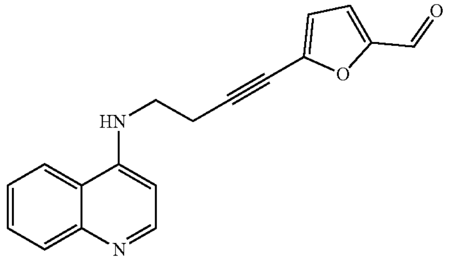

To a degassed solution of 5-bromofuran-2-carbaldehyde 6 (110 mg, 0.575 mmol, 1.2 equiv) in THF/$Et_3N$ (6 mL/2 mL), Pd[$PPh_3$]$_4$ (83.4 mg, 0.024 mmol, 0.15 equiv) and Cul (27.47 mg, 190.47 mmol, 0.3 equiv) were added. After degassing the reaction mixture for 5 min at room temperature, N-(but-3-yn-1-yl)quinolin-4-amine 10 (100 mg, 0.480 mmol, 1 equiv) was added dropwise and the reaction mixture was stirred at the room temperature for 16 h. Upon completion, the reaction mixture was concentrated under reduced pressure and the residue was purified by column chromatography (EtOAc to MeOH/$CH_2Cl_2$ 5:95) to afford the 5-(4-(quinolin-4-ylamino)but-1-yn-1-yl)furan-2-carbaldehyde 12 as an off white solid (115 mg, 81%); $R_f$ (10% MeOH/$CH_2Cl_2$) 0.25; $^1H$ NMR (400 MHz, $CD_3OD$): δ ppm 9.56 (s, 1H), 8.48 (d, J=8.4 Hz, 1H), 8.37 (d, J=6.3 Hz, 1H), 8.13 (d, J=8.5 Hz, 1H), 7.95 (s, 1H), 7.76-7.66 (m, 1H), 7.53-7.48 (m, 1H), 7.19 (d, J=3.7 Hz, 1H), 6.66-6.57 (m, 2H), 3.84 (q, J=6.5 Hz, 2H), 3.04 (t, J=6.9 Hz, 2H); $^{13}C$ NMR (101 MHz, $CD_3OD$): δ ppm 177.09, 152.10, 151.66, 147.35, 144.62, 144.28, 141.60, 130.79, 126.37, 125.76, 121.71, 121.24, 118.28, 116.70, 98.43, 94.80, 41.39, 19.95.

5-(4-(quinolin-4-ylamino)butyl)furan-2-carbaldehyde 13

13

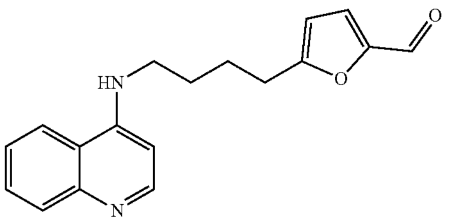

To a solution of 5-(4-(quinolin-4-ylamino)but-1-yn-1-yl) furan-2-carbaldehyde 12 (25 mg, 0.0861 mmol) in 3:1 ratio of EtOAc/MeOH (4 mL) was added 10% Pd/C (10 mg) at room temperature under Argon atmosphere and stirred the mixture for 2.5 h under $H_2$ using balloon pressure. Upon completion, the mixture was filtered using celite pad, concentrated under reduced pressure and the crude was purified by column chromatography (EtOAc to MeOH/$CH_2Cl_2$ 10:90) to afford 5-(4-(quinolin-4-ylamino)butyl)furan-2-carbaldehyde 13 as pale yellow solid (22 mg, 87%); $R_f$(10% MeOH/$CH_2Cl_2$) 0.20; IR (neat): $v_{max}$ 2926, 1666, 1579, 1514, 1339, 1119, 1021, 759, 538 $cm^{-1}$; HRMS (ESI$^+$): m/z calcd for $C_{18}H_{19}N_2O_2{}^+$295.144300 found 295.144104; $^1$H NMR (400 MHz, $CD_3OD$): δ ppm 9.42 (s, 1H), 8.33 (d, J=5.0 Hz, 1H), 8.10 (d, J=7.8 Hz, 1H), 7.80 (d, J=8.4 Hz, 1H), 7.65-7.62 (m, 1H), 7.58-7.51 (m, 1H), 7.46-7.41 (m, 1H), 7.33 (d, J=3.6 Hz, 1H), 6.50 (d, J=5.7 Hz, 1H), 6.38 (dd, J=3.6, 0.8 Hz, 1H), 3.40 (t, J=6.8 Hz, 2H), 2.82 (t, J=7.1 Hz, 2H), 1.91-1.74 (m, 4H); $^{13}$C NMR (101 MHz, $CD_3OD$): δ ppm 177.38, 163.77, 151.99, 151.56, 132.36, 131.72, 131.62, 129.36, 128.64, 128.52, 126.83, 124.36, 120.91, 108.88, 42.16, 27.41, 27.36, 24.85.

(E/Z)-5-(4-(quinolin-4-ylamino)butyl)furan-2-carbaldehyde oxime 14

14

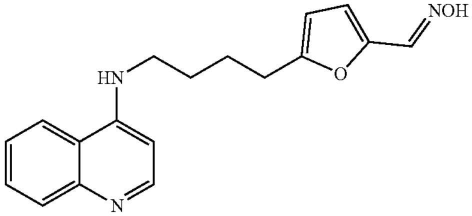

To a solution of 5-(4-(quinolin-4-ylamino)butyl)furan-2-carbaldehyde 13 (40 mg, 0.135 mmol) in EtOH (4 mL) was added TEA (54.9 mg, 0.543 mmol), hydroxylamine hydrochloride (18.89 mg, 0.271 mmol), and stirred at room temperature for 12 h. Upon completion, cooled to room temperature and distilled off under reduced pressure. The crude mixture was purified by column chromatography (MeOH/$CH_2Cl_2$, 1:9) to give cis-trans isomers of (1:0.4 ratio) of (E/Z)-5-(4-(quinolin-4-ylamino)butyl)furan-2-carbaldehyde oxime 14 as light brown solid (22 mg, 42%); $R_f$ (10% MeOH/$CH_2Cl_2$) 0.20; IR (neat): $V_{max}$ 3189, 3108, 2939, 2360, 2341, 1591, 1447, 1219, 976, 758 $cm^{-1}$; HRMS (ESI$^+$): m/z calcd for $C_{18}H_{20}N_3O_2{}^+$ 310.153453 found 310.155003; $^1$H NMR (400 MHz, $CD_3OD$): δ ppm 8.39 (t, J=8.3 Hz, 2H), 8.00-7.80 (m, 2.7H), 7.71 (t, J=7.5 Hz, 1H), 7.27 (s, 0.3H), 7.15 (d, J=4.2 Hz, 0.3H), 6.86 (d, J=6.6 Hz, 1H), 6.55 (d, J=3.2 Hz, 0.7H), 6.25(d, J=4.2 Hz, 0.3H), 6.19 (d, J=3.2 Hz, 0.7H), 3.62 (m, 2H), 2.78 (m, 2H), 1.86 (m, 4H); $^{13}$C NMR (101 MHz, $CD_3OD$): δ ppm 158.95, 157.64, 147.87, 143.05, 140.73, 139.29, 137.10, 134.82, 128.13, 123.81, 121.09, 119.40, 118.33, 114.34, 109.30, 108.67, 99.19, 44.41, 28.43, 28.39, 26.38, 26.27.

(E/Z)-5-(4-(quinolin-4-ylamino)butyl)furan-2-carbaldehyde oxime hydrochloride NM-80

NM-80

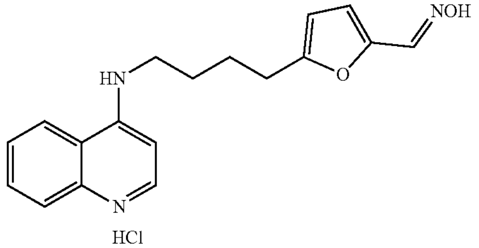

To a solution of (E/Z)-6-(2-(pyridin-3-yl)ethyl) pyridazine-3-carbaldehyde oxime 14 (20 mg, 0.064 mmol) in $H_2O$ (2 mL) was added 2N HCl (0.5 mL) at room temperature and stirred for 30 min at same temperature. Upon completion, solvent was distilled off under reduced pressure and the resulting solid was washed with diethyl ether (2×4 mL). The solid was dried under vacuum to give cis-trans isomers (60:40 ratio) of (E/Z)-5-(4-(quinolin-4-ylamino)butyl)furan-2-carbaldehyde oxime hydrochloride NM-80 as a light brown solid (18 mg, 80%); IR (neat): $v_{max}$ 2945, 2360, 1615, 1566, 1447, 1219, 758 $cm^{-1}$; $^1$H NMR (400 MHz, $CD_3OD$): δ ppm 8.45-8.30 (m, 2.4H), 8.03-7.81 (m, 2.6H), 7.71 (t, J=6.8 Hz, 1H), 7.22 (s, 0.6H), 6.86 (s, 1H), 6.56(d, J=2.8 Hz, 0.4H), 6.28 (d, J=7.6 Hz, 0.6H), 6.19 (d, J=2.6 Hz, 0.4H), 3.64 (s, 2H), 2.78 (s, 2H), 1.87 (s, 4H); $^{13}$C NMR (101 MHz, $CD_3OD$): δ ppm 159.06, 158.52, 157.65, 143.07, 139.23, 134.87, 128.16, 123.82, 121.07, 120.07, 118.32, 114.56, 109.67, 108.75, 99.25, 44.46, 28.50, 28.46, 28.43, 28.40, 26.38, 26.22.

(E/Z)-4-(2-(Pyridin-3-yl)ethyl)furan-2-carbaldehyde oxime FR-82

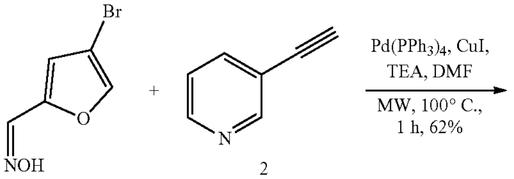

1 2

-continued

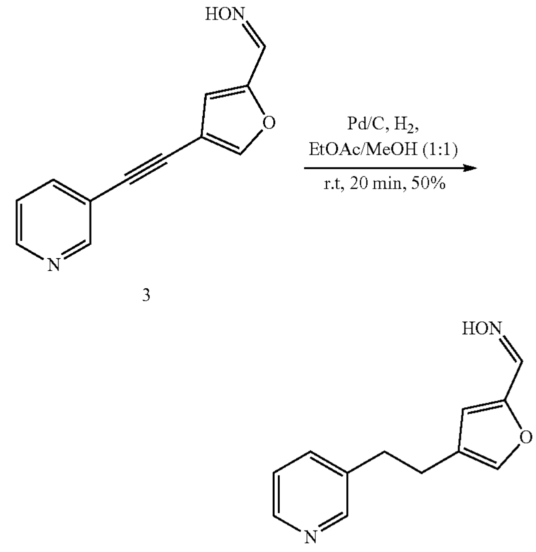

3

FR-82

(E/Z)-4-(pyridin-3-ylethynyl)furan-2-carbaldehyde oxime 3

3

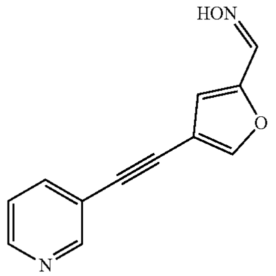

To a degassed solution of (E/Z)-4-bromofuran-2-carbaldehyde oxime 1 (80 mg, 0.421 mmol, 1 equiv) in DMF/$Et_3N$ (8 mL/2 mL), $Pd[PPh_3]_4$ (97.31 mg, 0.084 mmol, 0.2 equiv) and CuI (32.08 mg, 0.168 mmol, 0.4 equiv) were added. After degassing the reaction mixture for 5 min at room temperature, the alkyne (3-ethynylpyridine, 0.505 mmol, 1.2 equiv) was added dropwise and the reaction mixture was subjected to microwave irradiation for 1 hour at 100° C. After completion (monitored by TLC), the reaction mixture was concentrated under reduced pressure and the residue was purified by column chromatography (EtOAc/P 2:3) to afford the desired coupled (E/Z)-4-(pyridin-3-ylethynyl) furan-2-carbaldehyde oxime 3 as a yellow solid (55 mg, 62%). $R_f$ (50% EA+P) 0.3; $^1$H NMR (400 MHz, DMF-$d_7$) δ 12.39 (s, 0.6H), 11.75 (s, 0.4H), 8.77 (ddd, J=9.4, 2.3, 0.9 Hz, 1H), 8.63 (dd, J=4.9, 1.7 Hz, 1H), 8.27 (dd, J=7.6, 0.8 Hz, 1H), 8.12 (s, 0.4H), 7.99 (tt, J=8.6, 1.9 Hz, 1H), 7.60 (s, 0.6H), 7.52-7.47 (m, 1H), 7.42 (d, J=0.8 Hz, 0.6H), 6.97 (d, J=0.8 Hz, 0.4H). $^{13}$C NMR (101 MHz, DMF) δ 152.86, 152.83, 150.43, 150.26, 148.87, 147.94, 147.38, 139.57, 139.51, 139.49, 136.03, 124.70, 120.84, 119.03, 113.99, 110.01, 109.63, 89.26, 89.19, 84.21.

(E/Z)-4-(2-(pyridin-3-yl)ethyl)furan-2-carbaldehyde oxime FR-82

FR-82

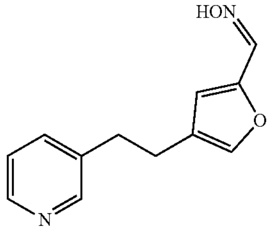

To a degassed solution of (E/Z)-4-(pyridin-3-ylethynyl) furan-2-carbaldehyde oxime (40 mg, 0.131 mmol, 1 equiv) in EtOAc/MeOH (3 mL/1 mL), Pd/C (14 mg (10% w), 0.013 mmol, 0.1 equiv) was added. After degassing the reaction mixture for 5 min at room temperature, the mixture is stirred under $H_2$ pressure for 1 h. After completion (monitored by TLC), the reaction mixture was concentrated under reduced pressure and the residue was purified by preparative chromatography (EtOAc/P 1:1) to afford the desired hydrogenated (E/Z)-4-(2-(pyridin-3-yl)ethyl)furan-2-carbaldehyde oxime FR-82 as a white solid (15 mg, 50%). $R_f$ (50% EA+P) 0.2; $^1$H NMR (400 MHz, DMF-$d_7$) δ 11.99 (s, 0.67H), 11.43 (s, 0.33H), 8.48 (d, J=30.9 Hz, 2H), 8.02 (s, 0.33), 7.71 (t, J=7.7 Hz, 1H), 7.55 (d, J=0.8 Hz, 0.67H), 7.53-7.50 (m, 0.34H), 7.45 (s, 0.67H), 7.33 (dd, J=7.4, 4.7 Hz, 1H), 7.25 (s, 0.67H), 6.70 (s, 0.33H), 2.95 (dd, J=8.8, 6.8 Hz, 2H), 2.86-2.77 (m, 2H). $^{13}$C NMR (101 MHz, DMF) δ 147.67, 146.12, 141.01, 140.26, 136.05, 135.93, 126.94, 118.03, 33.04, 29.06, 26.23.

(Z)-5-(2-(1-methyl-1H-imidazol-5-yl)ethyl)furan-2-carbaldehyde oxime hydrochloride FR-152

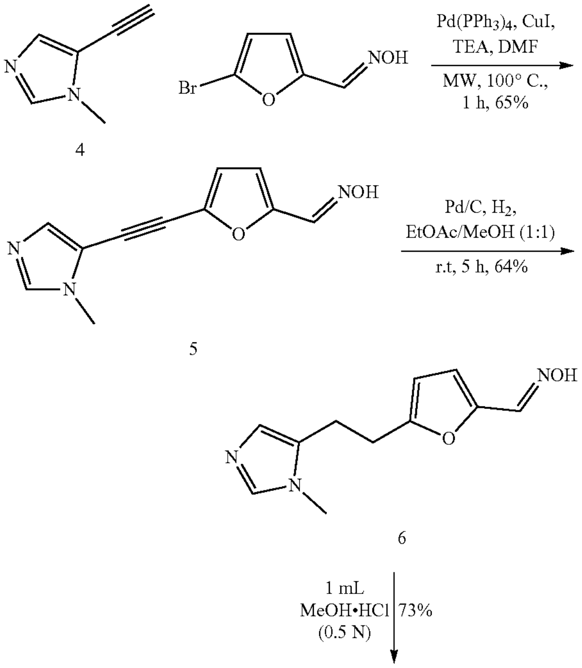

4

5

6

-continued

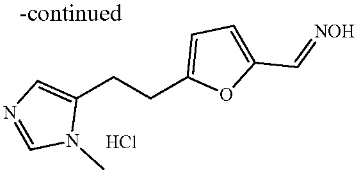

FR-152

(Z/E)-5-((1-methyl-1H-imidazol-5-yl)ethynyl)furan-2-carbaldehyde oxime 5

5

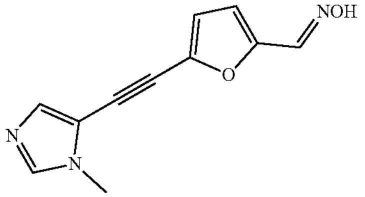

To a degassed solution of 5-bromofuran-2-carbaldehyde oxime 1 (100 mg, 0.526 mmol, 1 equiv) in DMF/$Et_3N$ (8 mL/2 mL), $Pd[PPh_3]_4$ (121.64 mg, 0.105 mmol, 0.2 equiv) and CuI (40.10 mg, 0.210 mmol, 0.4 equiv) were added. After degassing the reaction mixture for 5 min at room temperature, the alkyne 5-ethynyl-1-methyl-1H-imidazole (64.14 μL, 0.631 mmol, 1.2 equiv) was added dropwise and the reaction mixture was subjected to microwave irradiation for 1 hour at 100° C. After completion (monitored by TLC), the reaction mixture was concentrated under reduced pressure and the residue was purified by column chromatography (MeOH/EtOAc 5%) to afford the desired coupled (Z/E)-5-((1-methyl-1H-imidazol-5-yl)ethynyl)furan-2-carbaldehyde oxime 5 as a yellow solid (70 mg, 62%). $R_f$ (5% MeOH+EtOAc) 0.2; $^1$H NMR (400 MHz, Methanol-$d_4$) δ 7.97 (s, OH), 7.75 (s, 1H), 7.41 (s, 1H), 7.37-7.32 (m, 1H), 7.32 (d, J=3.6 Hz, 1H), 6.89 (dd, J=3.6, 0.6 Hz, 1H), 6.83 (d, J=3.6 Hz, OH), 6.72 (d, J=3.6 Hz, OH), 3.76 (d, J=1.9 Hz, 3H). $^{13}$C NMR (101 MHz, MeOD) δ 150.73, 147.87, 139.82, 138.05, 136.96, 136.05, 135.15, 135.06, 133.57, 132.92, 132.81, 129.83, 129.70, 124.31, 119.16, 118.83, 118.79, 117.68, 113.28, 86.81, 86.77, 82.48, 82.35, 49.43, 49.21, 49.00, 48.79, 48.58, 48.36, 48.15, 32.47, 32.38. HRMS ($ESI^+$) m/z calcd 216.07728 for $C_{11}H_{10}N_3O_2^+$ found 216.076753.

(E/Z)-5-(2-(1-methyl-1H-imidazol-5-yl)ethyl)furan-2-carbaldehyde oxime 6

6

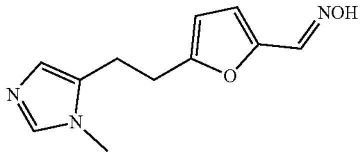

To a degassed solution of (Z/E)-5-((1-methyl-1H-imidazol-5-yl)ethynyl)furan-2-carbaldehyde oxime (20 mg, 0.092 mmol, 1 equiv) in EtOAc/MeOH (2 mL/2 mL), Pd/C (4.94 mg (10% w), 0.005 mmol, 0.05 equiv) was added. After degassing the reaction mixture for 5 min at room temperature, the mixture is stirred under $H_2$ pressure for 6 h. After completion (monitored by TLC), the reaction mixture was concentrated under reduced pressure and the residue was purified by preparative chromatography (MeOH/EtOAc 5%); to afford the desired hydrogenated (E/Z)-5-(2-(1-methyl-1H-imidazol-5-yl)ethyl)furan-2-carbaldehyde oxime 6 as a white solid (13 mg, 64%). $R_f$ (5% MeOH+EA) {0.16; 0.221; $^1$H NMR (400 MHz, Methanol-$d_4$) δ 7.91 (s, OH), 7.53 (s, 1H), 7.34 (s, 1H), 7.16 (d, J=3.3 Hz, 1H), 6.72 (s, 1H), 6.55 (d, J=3.3 Hz, OH), 6.24 (dd, J=3.3, 0.7 Hz, 1H), 6.17 (d, J=3.4 Hz, OH), 3.58 (d, J=2.8 Hz, 3H), 3.02-2.96 (m, 4H). $^{13}$C NMR (101 MHz, MeOD) δ 156.38, 155.44, 144.61, 139.30, 137.38, 135.71, 124.64, 118.01, 112.82, 108.27, 107.66, 30.10, 26.76, 21.74.

(Z)-5-(2-(1-methyl-1H-imidazol-5-yl)ethyl)furan-2-carbaldehyde oxime hydrochloride FR-152

FR-152

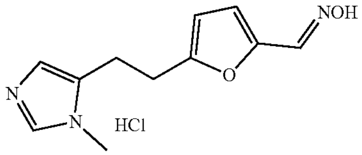

To a solution of (E/Z)-5-(2-(1-methyl-1H-imidazol-5-yl)ethyl)furan-2-carbaldehyde oxime (25 mg, 0.06 mmol) in MeOH (3 mL) was added 0.5N HCl (1 mL) at room temperature and stirred for 5 min at same temperature. Upon completion, solvent was distilled off under reduced pressure and the resulting solid was washed with diethyl ether (2×3 mL). The solid was dried under vacuum to give cis/trans isomer (6.5/3.5 ratio) of (E/Z)-2-(2-(pyridin-2-yl)ethyl)thiazole-4-carbaldehyde oxime hydrochloride FR-152 as a light brown solid (20 mg, 71%); $^1$H NMR (400 MHz, Chloroform-d) δ 8.76 (d, J=5.5 Hz, 1H), 7.87 (d, J=3.6 Hz, 0.35H), 7.50 (q, J=2.3 Hz, 0.65H), 7.24 (dt, J=9.3, 3.4 Hz, 1.65H), 6.53 (d, J=3.4 Hz, 0.35H), 6.34 (q, J=3.5, 3.0 Hz, 0.65H), 6.20 (d, J=3.3 Hz, 0.35H), 3.76 (dd, J=4.0, 2.2 Hz, 3H), 3.05 (dd, J=10.6, 3.8 Hz, 4H). $^{13}$C NMR (400 MHz, Methanol-$d_4$) δ 157.50, 156.88, 148.16, 145.69, 140.67, 137.21, 136.60, 135.75, 121.54, 117.85, 114.89, 110.82, 109.75, 33.75, 27.01, 26.94, 22.76, 22.65.

(3aS,4S,6R,6aR)-6-(6-amino-9H-purin-9-yl)-N-(4-(5-((Z)-(hydroxyimino)methyl)furan-2-yl)but-3-yn-1-yl)-2,2-dimethyltetrahydrofuro[3,4-d][1,3]dioxole-4-carboxamide FR-151

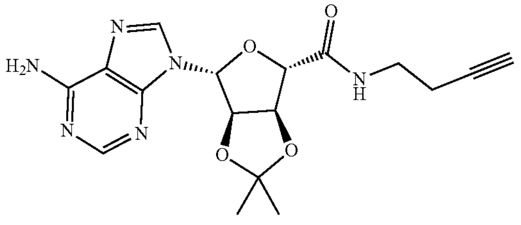

+

7

-continued

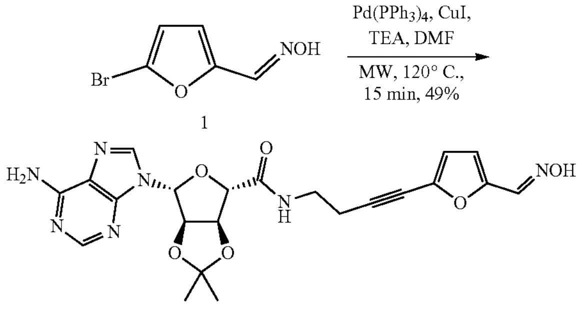

1

FR-151

To a degassed solution of (E/Z)-5-bromofuran-2-carbaldehyde oxime 1 (75 mg, 0.394 mmol, 1 equiv) in DMF/$Et_3N$ (8 mL/2 mL), $Pd[PPh_3]_4$ (22.81 mg, 0.019 mmol, 0.05 equiv) and CuI (3.76 mg, 0.019 mmol, 0.05 equiv) were added. After degassing the reaction mixture for 5 min at room temperature, the alkyne ((3aS,4S,6R,6aR)-6-(6-amino-9H-purin-9-yl)-N-(but-3-yn-1-yl)-2,2-dimethyltetrahydrofuro[3,4-d][1,3]dioxole-4-carboxamide 7, 0.505 mmol, 1.1 equiv) was added dropwise and the reaction mixture was subjected to microwave irradiation for 15 min at 120° C. After completion (monitored by TLC), the reaction mixture was concentrated under reduced pressure and the residue was purified by column chromatography (MeOH/EtOAc 2%) to afford the desired coupled oxime FR-151 (3aS,4S,6R,6aR)-6-(6-amino-9H-purin-9-yl)-N-(4-(5-((Z)-(hydroxyimino)methyl)furan-2-yl)but-3-yn-1-yl)-2,2-dimethyltetrahydrofuro[3,4-d][1,3]dioxole-4-carboxamide as a yellow solid (94 mg, 49%). $R_f$ (5% MeOH+EA) 0.25; $^1H$ NMR (400 MHz, Acetone-$d_6$) δ 11.19 (d, J=159.7 Hz, 1H), 8.26-8.16 (m, 2H), 7.70 (dt, J=36.8, 6.2 Hz, 1H), 6.94 (d, J=23.2 Hz, 2H), 6.65 (dd, J=6.1, 3.5 Hz, 1H), 6.36-6.31 (m, 1H), 5.50 (dd, J=6.3, 2.1 Hz, 1H), 5.46 (dt, J=6.1, 2.0 Hz, 1H), 4.63 (t, J=1.8 Hz, 1H), 3.27-3.15 (m, 2H), 2.50-2.20 (m, 2H), 1.57 (d, J=3.0 Hz, 3H), 1.36 (d, J=1.7 Hz, 3H). $^{13}C$ NMR (101 MHz, Acetone) δ 169.15, 169.12, 156.38, 152.87, 149.18, 148.42, 145.64, 140.54, 138.71, 137.71, 136.59, 135.19, 117.59, 116.49, 116.05, 113.58, 113.53, 112.19, 93.20, 91.01, 90.99, 90.94, 90.89, 86.72, 86.60, 83.92, 83.43, 83.36, 71.53, 71.49, 37.31, 37.25, 26.38, 26.35, 24.55, 19.47, 19.45.

(Z/E)-5-((3-hydroxyoxetan-3-yl)ethynyl)furan-2-carbaldehyde oxime FR-99

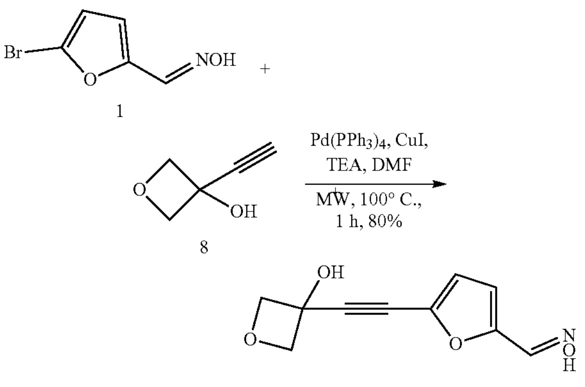

1

8

FR-99

To a degassed solution of (E/Z)-5-bromofuran-2-carbaldehyde oxime 1 (80 mg, 0.421 mmol, 1 equiv) in DMF/$Et_3N$ (8 mL/2 mL), $Pd[PPh_3]_4$ (97.31 mg, 0.084 mmol, 0.2 equiv) and CuI (32.08 mg, 0.168 mmol, 0.4 equiv) were added. After degassing the reaction mixture for 5 min at room temperature, the alkyne (3-ethynyloxetan-3-ol 8, 0.505 mmol, 1.2 equiv) was added dropwise and the reaction mixture was subjected to microwave irradiation for 1 hour at 100° C. After completion (monitored by TLC), the reaction mixture was concentrated under reduced pressure and the residue was purified by column chromatography (EtOAc/P 2:3) to afford the desired coupled oxime a(Z/E)-5-((3-hydroxyoxetan-3-yl)ethynyl)furan-2-carbaldehyde oxime FR-99 as a white solid (70 mg, 80%). IR (neat) $v_{m}$, x 753.11, 984.85, 1036.93, 1209.37, 1429.67, 2359.92, 3095.68. $R_f$ (50% EA+P) 0.30. $^1H$ NMR (400 MHz, Methanol-$d_4$) δ 7.97 (s, 1H), 7.41 (s, 0.3H), 7.30 (d, J=3.6 Hz, 0.27H), 6.82 (d, J=3.7 Hz, 0.27H), 6.76 (d, J=3.6 Hz, 1H), 6.70 (d, J=3.6 Hz, 1H), 4.91-4.87 (m, 2.7H), 4.76-4.70 (m, 2.7H). $^{13}C$ NMR (101 MHz, MeOD) δ 149.11, 146.35, 138.73, 136.81, 135.75, 117.55, 117.14, 112.01, 93.94, 93.82, 84.23, 84.21, 74.73, 66.50, 48.29, 48.08, 47.87, 47.66, 47.44, 47.23, 47.02. HRMS (ESI$^+$) m/z calcd 208.06096 for $C_{10}H_{11}NO_4^+$ found 208.060434.

(Z/E)-4-(5-phenylpent-1-yn-1-yl)furan-2-carbaldehyde oxime FR-66

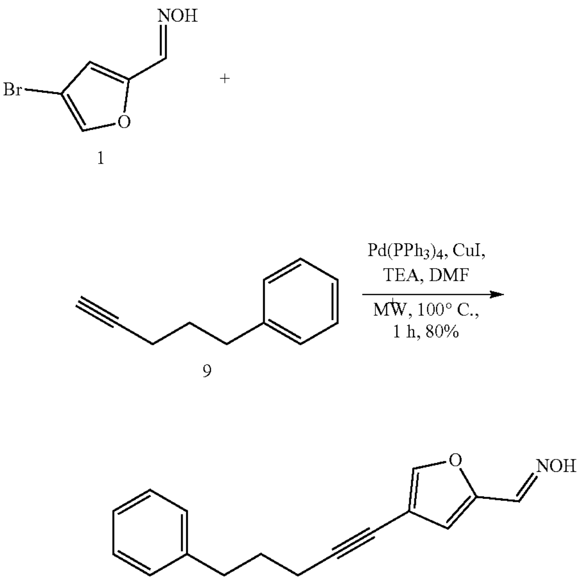

1

9

FR-66

To a degassed solution of (E/Z)-4-bromofuran-2-carbaldehyde oxime 1 (100 mg, 0.526 mmol, 1 equiv) in DMF/$Et_3N$ (8 mL/2 mL), $Pd[PPh_3]_4$ (121.64 mg, 0.105 mmol, 0.2 equiv) and CuI (40.1 mg, 0.210 mmol, 0.4 equiv) were added. After degassing the reaction mixture for 5 min at room temperature, the alkyne (pent-4-yn-1-ylbenzene 9, 0.578 mmol, 1.2 equiv) was added dropwise and the reaction mixture was subjected to microwave irradiation for 1 hour at 100° C. After completion (monitored by TLC), the reaction mixture was concentrated under reduced pressure and the residue was purified by column chromatography (EtOAc/P 10%) to afford the desired coupled (Z/E)-4-(5-phenylpent-1-yn-1-yl)furan-2-carbaldehyde oxime FR-66 as a white solid (80 mg, 60%). $R_f$ (10% EA+P) 0.25; $^1$H NMR (400 MHz, Chloroform-d) δ 7.96 (s, 0.6H), 7.59 (d, J=3.5 Hz, 1H), 7.42-7.27 (m, 2H), 7.26-7.11 (m, 3H), 6.64 (s, 1H), 2.78 (td, J=7.5, 2.7 Hz, 2H), 2.40 (td, J=7.1, 2.2 Hz, 2H), 1.92 (p, J=7.3 Hz, 2H). $^{13}$C NMR (101 MHz, $CDCl_3$) δ 147.09, 146.48, 145.52, 141.61, 141.58, 139.86, 128.66, 128.65, 128.51, 126.08, 126.07, 120.82, 115.17, 110.84, 110.17, 92.60, 92.44, 77.48, 77.16, 76.84, 71.22, 70.98, 34.96, 34.95, 30.24, 30.21, 18.95.

(Z/E)-5-(4-(1,3-dioxoisoindolin-2-yl)but-1-yn-1-yl)furan-2-carbaldehyde oxime CV-59

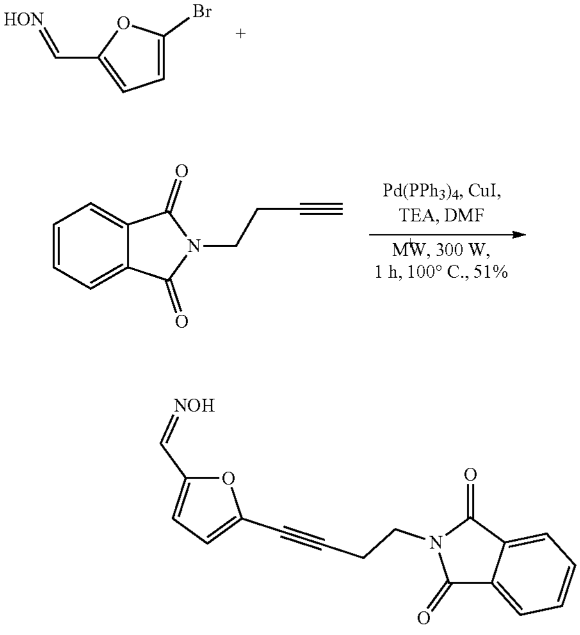

CV-59

To a degassed solution of (Z/E)-5-bromofuran-2-carbaldehyde oxime (50 mg, 0.263 mmol, 1 equiv) in DMF/$Et_3N$ (8 mL/2 mL), $Pd[PPh_3]_4$(61 mg, 0.053 mmol, 0.20 equiv) and CuI (20 mg, 0.105 mmol, 0.40 equiv) were added. After degassing the reaction mixture for 5 min at room temperature, the alkyne 2-(but-3-yn-1-yl)isoindoline-1,3-dione (63 mg, 0.316 mmol, 1.2 equiv) was added dropwise and the reaction mixture was subjected to microwave irradiation for 1 h at 100° C. After completion (monitored by TLC), the reaction mixture was concentrated under reduced pressure and the residue was purified by column chromatography (EtOAc/PE 30%) to afford the desired coupled oxime (Z/E)-5-(4-(1,3-dioxoisoindolin-2-yl)but-1-yn-1-yl)furan-2-carbaldehyde oxime CV-59 as a yellow solid (41 mg, 51%). $R_f$(50% EA+PE) 0.63; $^1$H NMR (400 MHz, $CDCl_3$) δ 7.91 (s, 0.5H), 7.86 (tt, J=5.4, 2.6 Hz, 2H), 7.76-7.69 (m, 2H), 7.42 (s, 0.5H), 7.35 (s, 0.5H), 6.57 (d, J=3.5 Hz, 0.5H), 6.55 (d, J=3.5 Hz, 0.5H), 6.49 (d, J=3.5 Hz, 0.5H), 3.96 (q, J=7.0 Hz, 2H), 2.87 (q, J=7.0 Hz, 2H). $^{13}$C NMR (101 MHz, $CDCl_3$) δ 168.13, 147.25, 139.96, 134.29, 134.27, 132.08, 123.58, 119.59, 117.17, 116.38, 113.23, 92.48, 92.39, 72.58, 72.53, 36.35, 19.67.

(Z/E)-5-(4-(1,3-dioxoisoindolin-2-yl)butyl)furan-2-carbaldehyde oxime CV-60

CV60

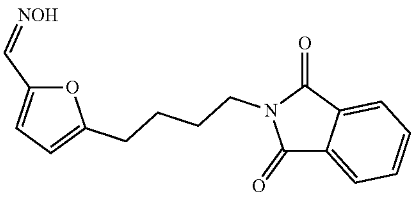

To a degassed solution of (Z/E)-5-(4-(1,3-dioxoisoindolin-2-yl)but-1-yn-1-yl)furan-2-carbaldehyde oxime CV-59 (29 mg, 0.094 mmol, 1 equiv) in EtOAc/MeOH (4 mL/2 mL), Pd/C (12 mg (10% w), 0.0094 mmol, 0.10 equiv) was added. After degassing the reaction mixture for 5 min at room temperature, the mixture is stirred under $H_2$ pressure for 2 h.

After completion (monitored by TLC), the reaction mixture was concentrated under reduced pressure and the residue was purified by preparative chromatography (EtOAc/PE 50%); to afford the desired hydrogenated (Z/E)-5-(4-(1,3-dioxoisoindolin-2-yl)butyl)furan-2-carbaldehyde oxime CV-60 as a white solid (26 mg, 90%). $R_f$(50% EA+PE) 0.63; $^1$H NMR (400 MHz, $CDCl_3$) δ 7.90 (s, 1H), 7.84 (dd, J=5.7, 2.8 Hz, 2H), 7.71 (d, J=2.8 Hz, 2.5H), 7.37-7.32 (m, 0.5H), 6.49 (d, J=3.3 Hz, 0.5H), 6.18 (s, 0.5H), 6.08 (d, J=3.3 Hz, 0.5H), 3.77-3.67 (m, 2H), 2.70 (t, J=6.9 Hz, 2H), 1.78-1.66 (m, 4H). $^{13}$C NMR (101 MHz, $CDCl_3$) δ 168.58, 158.31, 145.67, 134.09, 134.05, 132.21, 123.38, 123.36, 114.35, 107.62, 37.66, 28.12, 27.75, 25.25.

(Z/E)-5-(4-(1,3-dioxoisoindolin-2-yl)but-1-yn-1-yl)thiophene-2-carbaldehyde oxime CV-65

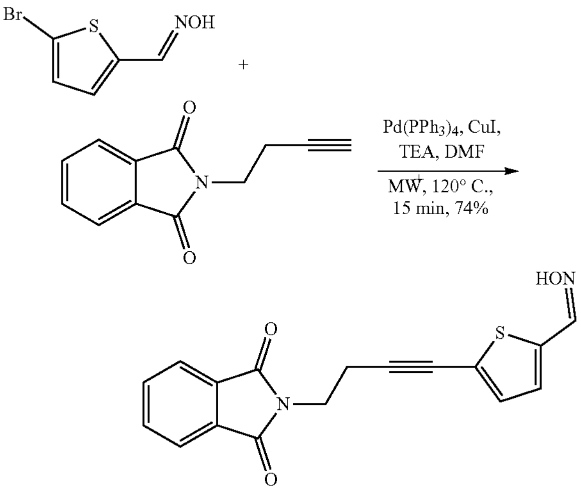

CV-65

To a degassed solution of (Z/E)-5-bromothiophene-2-carbaldehyde oxime (50 mg, 0.243 mmol, 1 equiv) in DM (8 mL) $Pd[PPh_3]_4$(14 mg, 0.012 mmol, 0.05 equiv), CuI (2 mg, 0.012 mmol, 0.05 equiv) and $Et_3N$ (101 μL, 0.728 mmol, 3 equiv) were added. After degassing the reaction mixture for 5 min at room temperature, the alkyne 2-(but-3-yn-1-yl) isoindoline-1,3-dione (58 mg, 0.291 mmol, 1.2 equiv) was added dropwise and the reaction mixture was subjected to microwave irradiation for 15 min at 120° C. After completion (monitored by TLC), the reaction mixture was concentrated under reduced pressure and the residue was purified by column chromatography (EtOAc/PE 15%) to afford the desired coupled oxime (Z/E)-5-(4-(1,3-dioxoisoindolin-2-yl)but-1-yn-1-yl)thiophene-2-carbaldehyde oxime CV-65 as a yellow solid (58 mg, 74%). $R_f$ (50% EA+PE) 0.57; $^1$H NMR (400 MHz, $CDCl_3$) δ 7.87 (ddd, J=5.4, 3.2, 1.0 Hz, 2H), 7.77-7.68 (m, 3H), 7.35 (d, J=4.2 Hz, 0.5H), 7.21 (d, J=3.9 Hz, 0.5H), 7.05 (d, J=3.8 Hz, 1H), 6.98 (s, 0.5H), 3.96 (td, J=7.1, 4.7 Hz, 2H), 2.86 (q, J=7.2 Hz, 2H $^{13}$C NMR (101 MHz, $CDCl_3$) δ 168.19, 144.69, 136.08, 134.26, 132.11, 129.30, 123.57, 123.55, 93.31, 92.23, 75.67, 36.56, 31.07, 19.95.

Example 2: in vitro reactivation of human acetyicholinesterase (hAChE) by compounds of the invention Compounds NM-27, 28, 29 and 34 and FR-152 of the invention were tested for their reactivation properties of hAChE inhibited by O-ethyl S-[2-(diisopropylamino)ethyl] methylphosphonothioate (VX), tabun, sarin or paraoxon. 2-PAM (pralidoxime or 2-[(E)-(hydroxyimino)methyl]-1-methylpyridinium) and HI6 (asoxime chloride or [1-[(4-carbamoylpyridin-1-ium-1-yl)methoxymethyl]pyridin-2-ylidene]methyl-oxoazanium dichloride) were used as comparative compounds.

Inhibition of hAChE by OPNAs. Recombinant hAChE was produced and purified as previously described (see reference https://www.ncbi.nlm.nih.gov/pubmed/31132435). VX, sarin and tabun have been supplied by DGA maitrise NRBC (Vert le Petit, France). Stock solutions of OPNA at 5 mM in isopropanol were used to inhibit the purified hAChE as previously described [Carletti, E. et al. 2008]. Briefly, a ten-fold excess of OPNA was used to perform the inhibition of hAChE in a sodium phosphate buffer (100 mM, pH 7.4, 0.1% BSA) at 25° C. Complete inhibition of hAChE was monitored by measuring the residual activity with a modified Ellman assay as previously described [Ellman, G. L., et al. 1961] and excess of OPNA were removed by using a desalting PD-10 column (GE Healthcare).

$IC_{50}$ measurements. Compounds were dissolved in water to make 40 mM stock solutions. Recombinant hAChE activity was measured spectrophotometrically at 25° C., monitoring the absorbance at 412 nm, in 1 mL of Ellman's buffer (0.5 mM DTNB, 0.1% BSA, 0.1 M phosphate, pH 7.4), in the presence of appropriate oxime concentrations. Measurements were performed at least in duplicate for each concentration tested. The oxime concentration producing 50% inhibition was determined by nonlinear fitting with ProFit (Quantumsoft) using the standard IC 50 equation: % activity=100×IC50/(IC50+[Ox]).

Reactivation of hAChE inhibited by OPNAs. The ability of the compounds to reactivate OP-inhibited hAChE were assessed with a modified Ellman assay using a microplate reader (SPARK 10M, Tecan) and a continuous method described previously [Kitz, R. J., et al. 1965, Worek, F., et al., 2004] with minor modifications. Briefly, the desired oximes concentrations to be tested were dispensed in a 96-well flat-bottomed polystyrene microplate containing 0.1% BSA phosphate buffer and DTNB. At t=0, OP-inhibited hAChE and acetylthiocholine (ATCh) diluted in 0.1% BSA phosphate buffer were injected in each well containing oximes using the built-in injectors of the microplate reader to a final volume of 200 μL. ATCh hydrolysis was continuously monitored over 30 minutes and the increase of absorbance at 412 nm recorded every 10 seconds at 25° C. Activities were individually corrected for oxime-induced hydrolysis of ATCh.

Reactivation of OP-inhibited hAChE by oximes proceeds according to scheme 1 and kinetics of oximes reactivation were determined as previously described [Worek, F., et al., 2004]. For each oxime concentration, the apparent reactivation rate, $k_{obs}$, the dissociation constant, $K_D$ and the reactivation rate constant, $k_r$, were calculated by nonlinear fitting with ProFit (Quantumsoft) using the standard oxime-concentration-dependent reactivation equation (1):

Scheme 1

$$[EP] + [OX] \overset{K_D}{\rightleftarrows} [EPOX] \overset{k_r}{\rightarrow} [E] + [POX] \quad \text{Eq (1)}$$

$$k_{obs} = \frac{k_r[OX]}{K_D + [OX]}$$

When [OX]«$K_D$, Eq (1) simplifies to Eq (2):

$$k_{obs} = \left(\frac{k_r}{K_n}\right)[OX] \quad \text{Eq (2)}$$

The second order reactivation rate constant $k_{r2}$, describing the specific reactivity can be derived from Eq (2).

$$k_{r2} = \frac{k_r}{K_D} \quad \text{Eq (3)}$$

For the continuous method of recording OP-inhibited hAChE reactivation by oximes, the velocity of substrate hydrolysis (v) is proportional to the concentration of the reactivated hAChE and is expressed and derived as equation 4 and 5 respectively. $v_t$, is the velocity at time t and $v0_0$ represents the maximum velocity. Equation 5 was used to determine the $k_{obs}$ by non-linear regression analysis for each individual oxime concentration with ProFit (Quantumsoft).

$$v_t = v_0(1 - e^{-kobst}): \quad \text{Eq (4)}$$

$$-d[S] = \int_0^t v dt = v_0 t + \frac{v_0}{k_{obs}}\left(e^{-k_{obs}t} - 1\right) \quad \text{Eq (5)}$$

The results are as follows:

TABLE 1

Reactivation of OP-inhibited human hAChE by oximes 2-PAM, HI-6, NMs and FR-152

| OP | Oximes | $k_r$ ($min^{-1}$) | $K_D$ (μM) | $K_{r2}$ ($mM^{-1} \cdot min^{-1}$) |
|---|---|---|---|---|
| VX | 2-PAM | 0.2 ± 0.01 | 26 ± 7 | 7 |
| | HI-6 | 0.4 ± 0.02 | 19 ± 4 | 20 |
| | NM27 | 0 | 0 | 0 |
| | NM28 | 0 | 0 | 0 |

TABLE 1-continued

Reactivation of OP-inhibited human hAChE by oximes 2-PAM, HI-6, NMs and FR-152

| OP | Oximes | $k_r$ ($min^{-1}$) | $K_D$ (μM) | $K_{r2}$ ($mM^{-1} \cdot min^{-1}$) |
|---|---|---|---|---|
| | NM29 | 0.08 ± 0.002 | 8 ± 0.6 | 10 |
| | NM34 | 0.09 ± 0.002 | 20 ± 2 | 4 |
| | FR-152 | 0.14 ± 0.003 | 7 ± 0.8 | 18 |
| Sarin | 2-PAM | 0.3 ± 0.02 | 25 ± 7 | 11 |
| | HI-6 | 0.8 ± 0.06 | 57 ± 11 | 13 |
| | NM27 | 0 | 0 | 0 |
| | NM28 | 0 | 0 | 0 |
| | NM29 | 0.1 ± 0.003 | 69 ± 26 | 1.4 |
| | NM34 | 0 | 0 | 0 |
| | FR-152 | 0.14 ± 0.005 | 16 ± 2 | 8.5 |
| Tabun | 2-PAM | 0.5 ± 0.2 | 211 ± 113 | 2 |
| | HI-6 | 0 | 0 | 0 |
| | NM27 | 0 | 0 | 0 |
| | NM28 | 0 | 0 | 0 |
| | NM29 | 0 | 0 | 0 |
| | NM34 | 0 | 0 | 0 |
| | FR-152 | 0 | | 0 |
| Paraoxon | 2-PAM | 0.07 ± 0.02 | 68 ± 16 | 1 |
| | HI-6 | 0.8 ± 0.06 | 290 ± 70 | 0.4 |
| | NM27 | 0 | 0 | 0 |
| | NM28 | 0 | 0 | 0 |
| | NM29 | 0.1 ± 0.04 | 12 ± 2 | 8 |
| | NM34 | 0.2 ± 0.034 | 10 ± 1 | 20 |
| | FR-152 | / | / | 0.09 |

TABLE 2

IC50 for hAChE of oximes: 2-PAM, HI-6, NMs and FR-152

| Oxime | IC50 (μM) |
|---|---|
| 2-PAM | 580 ± 28 |
| HI-6 | 82 ± 6 |
| NM27 | Nd* |
| NM28 | Nd* |
| NM29 | 360 ± 43 |
| NM34 | 2359 ± 537 |
| FR-152 | 54 ± 4 |

*Nd: not determined, due to low solubility when the concentration is higher than 500 μM These results showed that the compounds of the invention have a broad spectrum of reactivation of OPNA-inhibited AChE: particularly they show an increased efficacy for VX and paraoxon, and a good potency against sarin.

The invention claimed is:

1. A compound, or a salt thereof, selected from the group consisting of:

(E/Z)-5-(pyridin-3-ylethynyl)thiophene-2-carbaldehyde oxime 4:

4

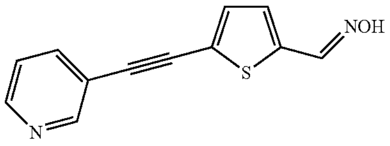

(E/Z)-5-(pyridin-3-ylethynyl)thiophene-2-carbaldehyde oxime hydrochloride NM-27:

NM-27

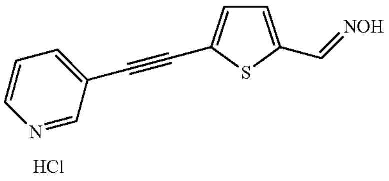

(E/Z)-5-(2-(pyridin-3-yl)ethyl)thiophene-2-carbaldehyde oxime 5:

5

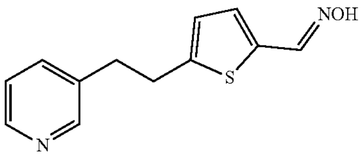

(E/Z)-5-(2-(pyridin-3-yl)ethyl)thiophene-2-carbaldehyde oxime hydrochloride NM-29:

NM-29

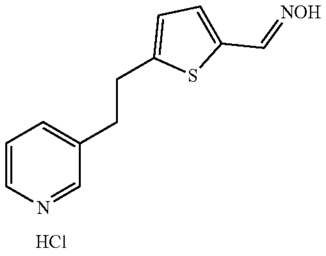

(E/Z)-5-(pyridin-3-ylethynyl)furan-2-carbaldehyde oxime 8:

8

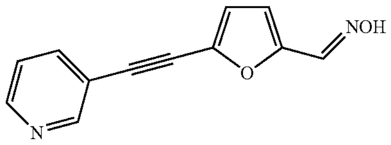

(E/Z)-5-(2-(pyridin-3-yl)ethyl)furan-2-carbaldehyde oxime 9:

9

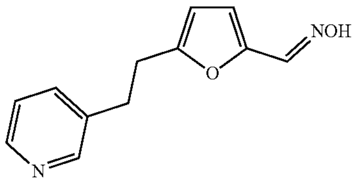

(E/Z)-5-(2-(pyridin-3-yl)ethyl)furan-2-carbaldehyde oxime hydrochloride NM-34:

NM-34

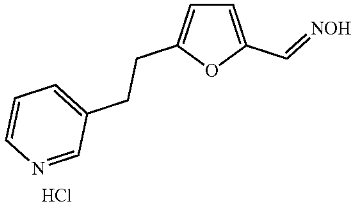

(E/Z)-5-(4-(quinolin-4-ylamino)but-1-yn-1-yl)furan-2-carbaldehyde oxime 11:

11

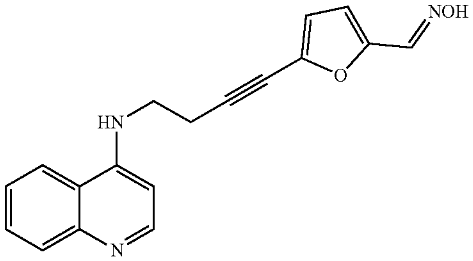

(E/Z)-5-(4-(quinolin-4-ylamino)but-1-yn-1-yl)furan-2-carbaldehyde oxime hydrochloride NM-53:

NM-53

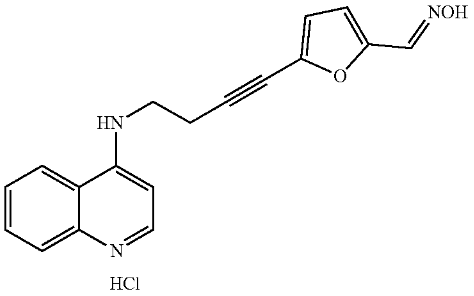

(E/Z)-5-(4-(quinolin-4-ylamino)butyl)furan-2-carbaldehyde oxime 14:

14

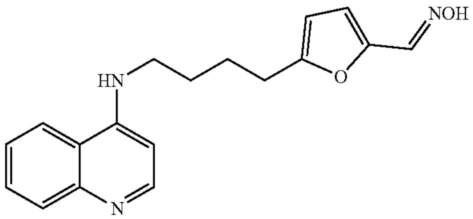

(E/Z)-5-(4-(quinolin-4-ylamino)butyl)furan-2-carbaldehyde oxime hydrochloride NM-80:

NM-80

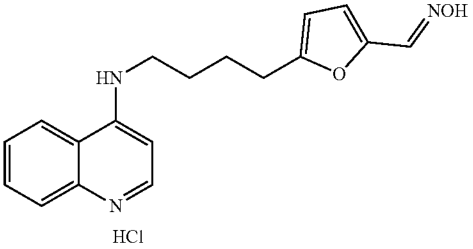

(Z/E)-5-(4-(1,3-dioxoisoindolin-2-yl)but-1-yn-1-yl)thiophene-2-carbaldehyde oxime CV-65:

CV-65

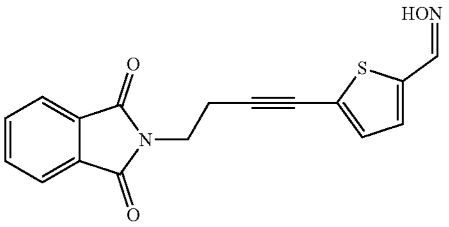

(Z/E)-5-((1-methyl-1H-imidazol-5-yl)ethynyl)furan-2-carbaldehyde oxime 5:

5

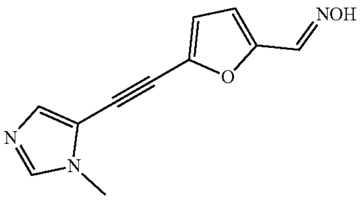

(E/Z)-5-(2-(1-methyl-1H-imidazol-5-yl)ethyl)furan-2-carbaldehyde oxime 6:

6

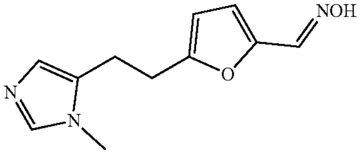

(Z)-5-(2-(1-methyl-1H-imidazol-5-yl)ethyl)furan-2-carbaldehyde oxime hydrochloride FR-152:

FR-152

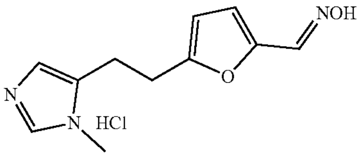

(3aS,4S,6R,6aR)-6-(6-amino-9H-purin-9-yl)-N-(4-(5-((Z)-(hydroxyimino)methyl)furan-2-yl)but-3-yn-1-yl)-2,2-dimethyltetrahydrofuro[3,4-d][1,3]dioxole-4-carboxamide FR-151:

FR-151

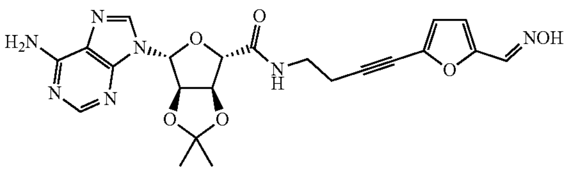

(Z/E)-5-((3-hydroxyoxetan-3-yl)ethynyl)furan-2-carbaldehyde oxime FR-99:

FR-99

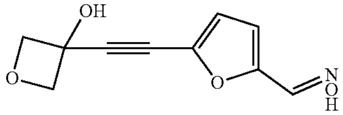

(Z/E)-5-(4-(1,3-dioxoisoindolin-2-yl)but-1-yn-1-yl) furan-2-carbaldehyde oxime CV-59:

CV-59

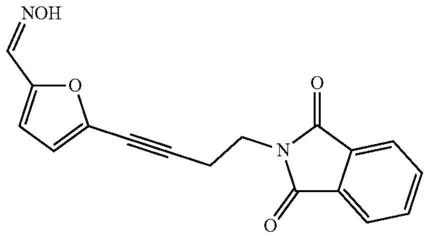

(Z/E)-5-(4-(1,3-dioxoisoindolin-2-yl)butyl)furan-2-carbaldehyde oxime CV-60

CV60

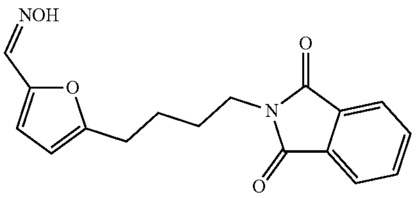

(E/Z)-4-(pyridin-3-ylethynyl)furan-2-carbaldehyde oxime 3:

3

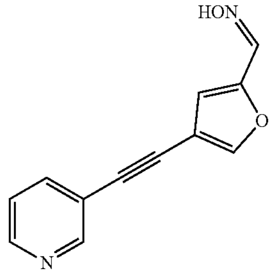

(E/Z)-4-(2-(pyridin-3-yl)ethyl)furan-2-carbaldehyde oxime FR-82:

FR-82

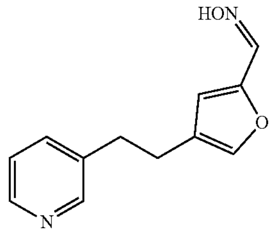

(Z/E)-4-(5-phenylpent-1-yn-1-yl)furan-2-carbaldehyde oxime FR-66:

FR-66

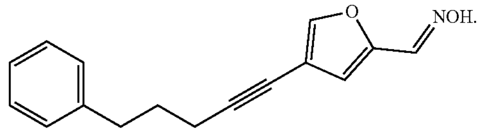

2. The compound of claim 1 formed as a hydrochloride salt.

3. A pharmaceutical composition comprising at least one compound according to claim 1, and at least one pharmaceutically acceptable flavorant, colorant, stabilizer, thickener, excipient, disintegrant, binder, or lubricant.

4. A process for preparing a compound according to claim 1, which comprises the following steps:

a Sonogashira coupling reaction between a terminal alkyne

and an isomer of unprotected bromo-thiophenoxime or an isomer of unprotected bromo-furanoxime, optionally under palladium catalysis, to obtain the conjugate

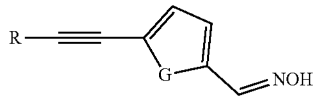

of formula (I), wherein G is O or S;

optionally, said conjugate is then submitted to hydrogenation, optionally with Pd/C catalyst in heterogeneous conditions, to provide the corresponding alkene, and finally the hybrid reactivator

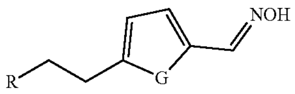

of formula (I), wherein G is O or S,

R being chosen from the following structures

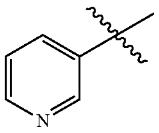

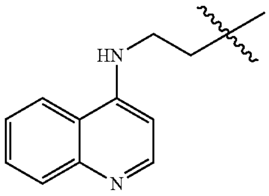

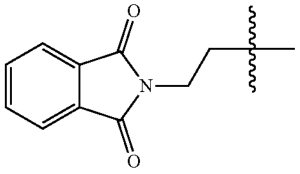

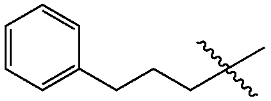

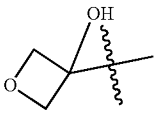

-continued

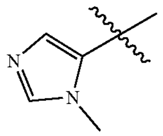

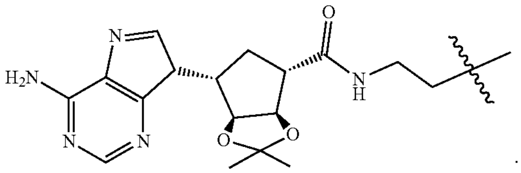

in which

represents the point of attachment to the alkyne.

5. A method for treating a nervous and/or respiratory failure due to intoxication with at least one organophosphorous nerve agent, by virtue of their reactivation potency of organophosphorous inhibited cholinesterases, including acetylcholinesterase and butyrylcholinesterase, in a subject in need thereof, comprising administering at least one compound according to claim 1 to said subject.

* * * * *